US012590889B2

(12) United States Patent
Hsiung et al.

(10) Patent No.: US 12,590,889 B2
(45) Date of Patent: Mar. 31, 2026

(54) OUTLIER DETECTION FOR SPECTROSCOPIC CLASSIFICATION

(71) Applicant: VIAVI Solutions Inc., Chandler, AZ (US)

(72) Inventors: Chang Meng Hsiung, Redwood City, CA (US); Lan Sun, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 0 days.

(21) Appl. No.: 18/311,989

(22) Filed: May 4, 2023

(65) Prior Publication Data

US 2023/0273121 A1 Aug. 31, 2023

Related U.S. Application Data

(63) Continuation of application No. 17/248,333, filed on Jan. 20, 2021, now Pat. No. 11,656,174, which is a
(Continued)

(51) Int. Cl.
| | |
|---|---|
| *G01N 21/35* | (2014.01) |
| *G01J 3/10* | (2006.01) |
| *G01N 21/25* | (2006.01) |
| *G01N 21/359* | (2014.01) |
| *G06F 18/2411* | (2023.01) |

(Continued)

(52) U.S. Cl.
CPC .............. *G01N 21/35* (2013.01); *G01J 3/108* (2013.01); *G01N 21/253* (2013.01); *G01N 21/359* (2013.01); *G06F 18/2411* (2023.01);

100 →

*G06F 18/2433* (2023.01); *G06N 20/00* (2019.01); *G06V 20/698* (2022.01); *G16C 20/20* (2019.02);
(Continued)

(58) Field of Classification Search
CPC ............. G06K 9/00147; G06K 9/6284; G06K 9/2018; G16C 20/70
See application file for complete search history.

(56) References Cited

U.S. PATENT DOCUMENTS

| | | | |
|---|---|---|---|
| 4,673,289 | A | 6/1987 | Gaucher |
| 7,133,710 | B2 | 11/2006 | Acosta et al. |

(Continued)

FOREIGN PATENT DOCUMENTS

| | | | |
|---|---|---|---|
| CN | 101504363 | A | 8/2009 |
| CN | 103364359 | A | 10/2013 |

(Continued)

OTHER PUBLICATIONS

Michiel Debruyne, "An Outlier Map for Support Vector Machine Classification", vol. 3, No. 4, 1566-1580 2009 (Year: 2009).*
(Continued)

*Primary Examiner* — Maurice C Smith
(74) *Attorney, Agent, or Firm* — Harrity & Harrity, LLP

(57) ABSTRACT

In some implementations, a device may determine that an unknown sample is an outlier sample by using an aggregated classification model. The device may determine that one or more spectroscopic measurements are not performed accurately based on determining that the unknown sample is the outlier sample. The device may cause one or more actions based on determining the one or more spectroscopic measurements are not performed accurately.

20 Claims, 13 Drawing Sheets

Related U.S. Application Data continuation-in-part of application No. 17/072,437, filed on Oct. 16, 2020, now Pat. No. 11,656,175, which is a continuation of application No. 16/130,732, filed on Sep. 13, 2018, now Pat. No. 10,810,408.

(60) Provisional application No. 62/622,637, filed on Jan. 26, 2018.

(51) Int. Cl.

| | |
|---|---|
| *G06F 18/2433* | (2023.01) |
| *G06N 20/00* | (2019.01) |
| *G06V 20/69* | (2022.01) |
| *G16C 20/20* | (2019.01) |
| *G16C 20/70* | (2019.01) |

(52) U.S. Cl.

CPC ....... *G16C 20/70* (2019.02); *G01N 2201/129* (2013.01)

(56) References Cited

U.S. PATENT DOCUMENTS

| | | | |
|---|---|---|---|
| 7,873,205 | B2 | 1/2011 | Okuda et al. |
| 8,189,892 | B2 | 5/2012 | Dimirova et al. |
| 9,435,728 | B2 | 9/2016 | Tsukii et al. |
| 9,513,167 | B2 | 12/2016 | Hargreaves et al. |
| 9,824,434 | B2 | 11/2017 | Tzao et al. |
| 10,309,894 | B2 | 6/2019 | Hsiung et al. |
| 10,401,312 | B2 | 9/2019 | Takis et al. |
| 10,489,550 | B2 | 11/2019 | Roder et al. |
| 10,810,408 | B2 | 10/2020 | Hsiung et al. |
| 10,839,527 | B2 | 11/2020 | Zhang et al. |
| 11,009,452 | B2 | 5/2021 | Hsiung |
| 11,461,690 | B2 | 10/2022 | Szeto et al. |
| 12,099,003 | B2 | 9/2024 | Hsiung et al. |
| 2003/0028358 | A1 | 2/2003 | Niu et al. |
| 2004/0077950 | A1 | 4/2004 | Marshik-Geurts et al. |
| 2005/0124074 | A1 | 6/2005 | Shelley et al. |
| 2007/0008523 | A1 | 1/2007 | Kaye et al. |
| 2007/0148697 | A1 | 6/2007 | Delaney et al. |
| 2007/0192035 | A1 | 8/2007 | Schweitzer et al. |
| 2010/0211329 | A1 | 8/2010 | Farquharson et al. |
| 2010/0217537 | A1 | 8/2010 | Neiss et al. |
| 2011/0237446 | A1 | 9/2011 | Treado et al. |
| 2012/0034647 | A1 | 2/2012 | Herzog et al. |
| 2012/0134559 | A1 | 5/2012 | Suzuki et al. |
| 2013/0256534 | A1 | 10/2013 | Micheels et al. |
| 2013/0311136 | A1 | 11/2013 | Blonshine et al. |
| 2015/0066377 | A1 | 3/2015 | Parchen et al. |
| 2015/0102216 | A1 | 4/2015 | Roder et al. |
| 2015/0154286 | A1 | 6/2015 | Lightner et al. |
| 2015/0204833 | A1 | 7/2015 | O'Brien et al. |
| 2016/0127405 | A1 | 5/2016 | Kasahara |
| 2018/0365535 | A1 | 12/2018 | Gesley et al. |
| 2021/0034838 | A1 | 2/2021 | Hsiung et al. |
| 2021/0142038 | A1 | 5/2021 | Hsiung et al. |
| 2021/0215597 | A1 | 7/2021 | Hsiung |
| 2022/0405644 | A1 | 12/2022 | Szeto et al. |

FOREIGN PATENT DOCUMENTS

| | | |
|---|---|---|
| CN | 105829869 A | 8/2016 |
| CN | 106483083 A | 3/2017 |
| CN | 106772417 A | 5/2017 |
| CN | 107229819 A | 10/2017 |
| CN | 107480690 A | 12/2017 |
| CN | 107561024 A | 1/2018 |
| EP | 1992939 A1 | 11/2008 |
| EP | 3136270 A1 | 3/2017 |
| JP | S6113139 A | 1/1986 |
| JP | H07234941 A | 9/1995 |
| JP | 2003139693 A | 5/2003 |
| JP | 2004294360 A | 10/2004 |
| JP | 2005534428 A | 11/2005 |
| JP | 2009276967 A | 11/2009 |
| JP | 2010527017 A | 8/2010 |
| JP | 2011027656 A | 2/2011 |
| JP | 2013535686 A | 9/2013 |
| JP | 2017049246 A | 3/2017 |
| JP | 2018040787 A | 3/2018 |
| JP | 2019522802 A | 8/2019 |
| JP | 2019526851 A | 9/2019 |
| TW | I284200 B | 7/2007 |
| TW | 200741192 A | 11/2007 |
| TW | 201504614 A | 2/2015 |
| TW | 201546640 A | 12/2015 |
| TW | 201617030 A | 5/2016 |
| TW | 201709110 A | 3/2017 |
| TW | 201802709 A | 1/2018 |
| WO | 2004012586 A2 | 2/2004 |
| WO | 2005069188 A1 | 7/2005 |
| WO | 2006056024 A1 | 6/2006 |
| WO | 2011077765 A1 | 6/2011 |
| WO | 2012019118 A1 | 2/2012 |
| WO | 2014165331 A1 | 10/2014 |
| WO | 2015080001 A1 | 6/2015 |
| WO | 2016139649 A2 | 9/2016 |
| WO | 2017127822 A1 | 7/2017 |
| WO | 2017136464 A1 | 8/2017 |
| WO | 2017174580 A1 | 10/2017 |
| WO | 2018017467 A1 | 1/2018 |

OTHER PUBLICATIONS

Forni O., et al., "Independent Component Analysis Classification of Laser Induced Breakdown Spectroscopy Spectra, "Spectrochimia Acta Part B, 2013, vol. 86, pp. 31-41.

Shengnan W., et al., "Outlier Sample Analysis on Near Infrared Spectroscopy Determination for Flour Ash, "2013 Fifth Conference on Measuring Technology and Mechatronics Automation, 2013, pp. 781-784.

Unnikrishnan V.K., et al., "Analytical Predictive Capabilities of Laser Induced Breakdown Spectroscopy (LIBS) With Principal Component Analysis (PCA) for Plastic Classification, "RSC Advances, 2013, vol. 3, pp. 25872-25880.

Peng D., et al., "Detection and Quantification of Adulteration of Sesame Oils with Vegetable Oil using Gas 1 Chromatography and Multivariate Data Analysis," Food Chemistry, 2015, vol. 188, pp. 415-421. DOI: 10.1016/j.foodchem.2015.05.001. Available on the Internet at URL: https://doi.org/10.1016/j.foodchem.2015.05.001.

Extended European Search Report for Application No. EP23157642. 2, mailed on May 24, 2023, 8 pages.

Aggarwal C.C., "Chapter 1 An Introduction to Outlier Analysis," Outlier Analysis, Second Edition, Nov. 25, 2016, Springer International Publishing, pp. 1-34. XP055597620.

Baassou et al., "An Accurate SVM-based Classification Approach for Hyperspectral Image Classification," International Conference on Geoinformatics, Jun. 2013, pp. 1-7.

Dubuisson B., et al., "A Statistical Decision Rule With Incomplete Knowledge About Classes," Pattern Recognition, Jan. 1993, vol. 26 (1), pp. 155-165. XP055568901.

Extended European Search Report for Application No. EP19150264. 0, mailed on Jun. 26, 2019, 12 pages,.

Extended European Search Report for Application No. EP19150386. 1, mailed on Jul. 1, 2019, 8 pages.

Extended European Search Report for Application No. EP21204170. 1, mailed on Apr. 14, 2022, 10 pages.

Haiyan Fu., et al., "A Comprehensive Quality Evaluation Method by FT-NIR Spectroscopy and Chemometric: Fine classification and Untargeted Authentication Against Multiple Frauds For Chinese Ganoderma Lucidum," Spectrochim Acta A Mol Biomol Spectrosc, 2017, vol. 182, pp. 17-25.

Hanczar B., et al., "Combination of One-Class Support Vector Machines for Classification with Reject Option," Joint European Conference on Machine Learning and Knowledge Discovery in Databases, Part 1, Lecture Notes in Computer Science, Sep. 2014, vol. 8724, pp. 547-562. XP047297812.

(56)          References Cited

OTHER PUBLICATIONS

Jiyu Peng., et al., "Fast Detection of Tobacco Mosaic Virus Infected Tobacco Using Laser Induced Breakdown Spectroscopy," Scientific Reports, 2017, vol. 7, pp. 44551.

Lascola et al., "A Piecewise Local Partial Least Squares (PLS) Method for the Quantitative Analysis of Plutonium Nitrate Solutions," Applied Spectroscopy, 2017, vol. 71 (12), pp. 2579-2594.

Maniruzzaman et al., "Accurate Diabetes Risk Stratification Using Machine Learning: Role of Missing Value and Outliers," Journal of Medical Systems, Springer, Apr. 10, 2018, vol. 42 (5), pp. 1-17, XP036507803.

Mertens., "Transformation, Normalization and Batch Effect in the Analysis of Mass Spectrometry Data for Omics Studies," Department of Medical Statistics, Leiden University Medical Center, Jun. 20, 2016, pp. 1-34.

Pasquini C., "Near Infrared Spectroscopy: A Mature Analytical Technique With New Perspectives—A Review," Analytica Chimica Acta, Oct. 2018, vol. 1026, pp. 8-36. XP055597813.

Quan H., et al., "Estimate of standard deviation for a log-transformed variable using arithmetic means and standard deviations," Statistics in Medicine, 2003, vol. 22, pp. 2723-2736.

Scholkopf B., et al., "Estimating the Support of a High-Dimensional Distribution," Neural Computation, Jul. 2001, vol. 13 (7), pp. 1443-1471. Retrieved from Internet: [URL:https://www.mitpressjournals.org/doi/abs/10.1162/089976601750264965]. XP055092861.

Smith-Moritz A. M., et al., "Combining Multivariate Analysis And Monosaccharide Composition Modeling to Identify Plant Cell Wall Variations By Fourier Transform Near Infrared spectroscopy," Plant Methods, 2011, vol. 7, pp. 26.

Sun et al., "Pharmaceutical Raw Material Identification Using Miniature Near-Infrared (MicroNIR) Spectroscopy and Supervised Pattern Recognition Using Support Vector Machine," Applied Spectroscopy, Mar. 2016, vol. 70 (5), pp. 816-825, XP055429869.

Tao B., et al., "Implementing Multi-Class Classifiers by One-Class Classification Methods," The 2006 IEEE International Joint Conference on Neural Network, IEEE Operations Center, Piscataway, NJ, USA, Jul. 2006, pp. 327-332. XP010948000.

Tax D.M.J., et al., "Support Vector Domain Description," Pattern Recognition Letters, Nov. 1999, vol. 20 (11-13) pp. 1191-1199. XP004490753.

Eo S.H., et al., "Outlier Detection using Projection Quantile Regression for Mass Spectrometry Data with Low Replication," BMC Research Notes, May 2012, vol. 5 (1), 9 pages, XP021129869.

Flem B., et al., "In Situ Analysis of Trace Elements in Quartz Using Laser Ablation Inductively Coupled Plasma Mass Spectrometry," In: Quartz: Deposits, Mineralogy and Analytics, Springer Geology, Jan. 2012, pp. 219-236. XP093069925, DOI:10.1007/978-3-642-22161-3_10.

Liu Z.C., et al., "Outlier Detection in Near-infrared Spectroscopic Analysis by Using Monte Carlo Cross-validation," Science in China Series B: Chemistry, Jul. 2008, vol. 51(8), pp. 751-759, XP055574331.

Changlong, W., et al., "Similar Spectrum Matching Prediction Soil Organic Matter and Cation Exchange," Transactions of the Chinese Society of Agricultural Engineering, vol. 30(1), pp. 81-88, Jan. 1, 2014.

Dan, L., et al., "Based on Multi-classifier C5.0 Decision Tree Vegetation Classification Method Law," Journal of Graphics, vol. 38(5), pp. 722-72815 Oct. 2017.

Yun, X., et al., "Based on Near Infrared Spectroscopy Clustering Method for Samples with Known Categories," Transactions of the Chinese Society of Agricultural Engineering, vol. 27(8), pp. 345-349 Aug. 2011.

Nie, P., et al., "Potential of Visible and Near Infrared Spectroscopy and Pattern Recognition for Rapid Quantification of Notoginseng Powder with Adulterants," Sensors, vol. 13(10), p. 13820-13834, Oct. 14, 2013. doi: 10.3390/s131013820.

Efenberger-Szmechtyk M., et al., "Implementation of Chemometrics in Quality Evaluation of Food and Beverages," Critical Reviews in Food Science and Nutrition, Jul. 2017, vol. 58(10), pp. 1747-1766.

Heibati, M., et al., "Assessment of Drinking Water Quality at the Tap Using Fluorescence Spectroscopy," Water Research, vol. 125 (2017), pp. 1-10, http://dx.doi.Org/10.1016/j.watres.2017.08.020.

* cited by examiner

100

Training set and validation set

Perform spectroscopic measurements

Spectrometer

Spectroscopic measurements

Perform spectroscopic measurements on the training set and the validation set

Control Device

Generate a classification model based on the spectroscopic measurements

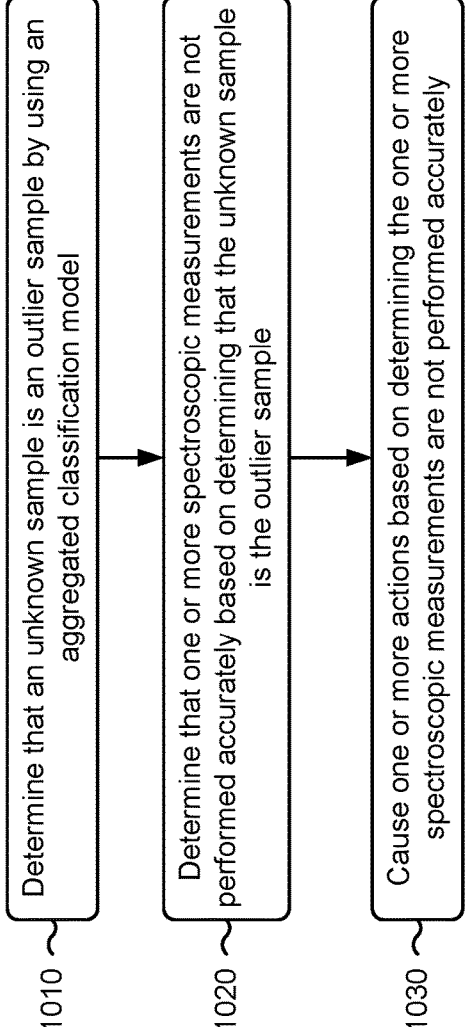

1010 — Determine that an unknown sample is an outlier sample by using an aggregated classification model 1020 — Determine that one or more spectroscopic measurements are not performed accurately based on determining that the unknown sample is the outlier sample 1030 — Cause one or more actions based on determining the one or more spectroscopic measurements are not performed accurately

OUTLIER DETECTION FOR SPECTROSCOPIC CLASSIFICATION

RELATED APPLICATIONS

The present application is a continuation of U.S. patent application Ser. No. 17/248,333, filed Jan. 20, 2021, entitled "OUTLIER DETECTION FOR SPECTROSCOPIC CLAS-SIFICATION," which is a continuation-in-part of U.S. patent application Ser. No. 17/072,437, filed Oct. 16, 2020, entitled "REDUCED FALSE POSITIVE IDENTIFICA-TION FOR SPECTROSCOPIC CLASSIFICATION," which is a continuation of U.S. patent application Ser. No. 16/130,732, filed Sep. 13, 2018, entitled "REDUCED FALSE POSITIVE IDENTIFICATION FOR SPECTRO-SCOPIC CLASSIFICATION," (now U.S. Pat. No. 10,810, 408), which claims priority to U.S. Provisional Patent Appli-cation No. 62/622,637, filed on Jan. 26, 2018, entitled "REDUCED FALSE POSITIVE IDENTIFICATION FOR SPECTROSCOPY," the contents of which are incorporated by reference herein in their entireties.

BACKGROUND

Raw material identification may be utilized for quality-control of pharmaceutical products. For example, raw mate-rial identification may be performed on a medical material to determine whether component ingredients of the medical material correspond to a packaging label associated with the medical material. Similarly, raw material quantification may be performed to determine a concentration of a particular chemical in a particular sample. Spectroscopy may facilitate non-destructive raw material identification and/or quantifi-cation with reduced preparation and data acquisition time relative to other chemometric techniques.

SUMMARY

According to some possible implementations, a method includes determining, by a device, that an unknown sample is an outlier sample by using an aggregated classification model; determining, by the device, that one or more spec-troscopic measurements are not performed accurately based on determining that the unknown sample is the outlier sample; and causing, by the device, one or more actions based on determining the one or more spectroscopic mea-surements are not performed accurately.

According to some possible implementations, a device includes one or more memories; and one or more processors, communicatively coupled to the one or more memories, to: receive information identifying results of a set of spectro-scopic measurements of a training set of known samples and a validation set of known samples; generate a classification model based on the information identifying the results of the set of spectroscopic measurements, the classification model including at least one class relating to a material of interest for a spectroscopic determination, the classification model including a no-match class relating to at least one of at least one material that is not of interest or a baseline spectroscopic measurement; receive information identifying a particular result of a particular spectroscopic measurement of an unknown sample; perform a first evaluation of the classifi-cation model on the unknown sample; identify, based on the first evaluation, an outlier sample is present in the classifi-cation model; remove the outlier sample from the classifi-cation model; perform a second evaluation of the classifi-cation model on the unknown sample based on removing the outlier sample from the classification model; and provide output indicating whether the unknown sample is included in the no-match class based on performing the second evaluation of the classification model.

According to some possible implementations, a non-transitory computer-readable medium storing instructions includes one or more instructions that, when executed by one or more processors, cause the one or more processors to: receive information identifying results of a spectroscopic measurement performed on an unknown sample; aggregate a plurality of classes of a classification model to generate an aggregated classification model; determine that the spectro-scopic measurement is performed accurately using the aggregated classification model; determine a confidence measure for a set of classes of the aggregated classification model; select a subset of the set of classes based on the confidence measure for the set of classes; generate an in situ local classification model using the subset of the set of classes; identify one or more outlier samples in the in situ local classification model; remove the one or more outlier samples from the in situ local classification model; generate a prediction using the in situ local classification model based on removing the one or more outlier samples; and provide an output identifying the prediction.

According to some possible implementations, a device may include one or more memories and one or more processors, communicatively coupled to the one or more memories. The device may receive information identifying results of a set of spectroscopic measurements of a training set of known samples and a validation set of known samples. The device may generate a classification model based on the information identifying the results of the set of spectroscopic measurements, wherein the classification model includes at least one class relating to a material of interest for a spectroscopic determination, and wherein the classification model includes a no-match class relating to at least one of at least one material that is not of interest or a baseline spectroscopic measurement. The device may receive infor-mation identifying a particular result of a particular spec-troscopic measurement of an unknown sample. The device may determine whether the unknown sample is included in the no-match class using the classification model. The device may provide output indicating whether the unknown sample is included in the no-match class.

According to some possible implementations, a non-transitory computer-readable medium may store one or more instructions that, when executed by one or more processors, cause the one or more processors to receive information identifying results of a spectroscopic measurement per-formed on an unknown sample. The one or more instruc-tions, when executed by the one or more processors, may cause the one or more processors to aggregate a plurality of classes of a classification model to generate an aggregated classification model. The one or more instructions, when executed by the one or more processors, may cause the one or more processors to determine that the spectroscopic measurement is performed accurately using the aggregated classification model. The one or more instructions, when executed by the one or more processors, may cause the one or more processors to determine, based on determining that the spectroscopic measurement is performed accurately and using the classification model, that the unknown sample is not included in a no-match class of the classification model, wherein the no-match class relates to material that is not of interests or baseline spectroscopic measurements. The one or more instructions, when executed by the one or more processors, may cause the one or more processors to perform, based on determining that the unknown sample is not included in the no-match class, a spectroscopic classification of the unknown sample. The one or more instructions, when executed by the one or more processors, may cause the one or more processors to provide information identifying the unknown sample based on performing the spectroscopic classification of the unknown sample.

According to some possible implementations, a method may include obtaining, by a device, results of a set of spectroscopic measurements. The method may include generating, by the device, a support vector machine (SVM)-based classification model based on the results of the set of spectroscopic measurements, the classification model including a plurality of classes corresponding to a plurality of materials of interest for classification, wherein the set of spectroscopic measurements include a threshold quantity of measurements of samples of the plurality of materials of interest, wherein the classification model includes a particular class not corresponding to the plurality of materials of interest for classification, and wherein the set of spectroscopic measurements includes less than the threshold quantity of measurements of samples relating to the particular class. The method may include classifying, by the device, a particular spectroscopic measurement of a particular sample to the particular class using the classification model. The method may include providing, by the device, information indicating that the particular sample is assigned to the particular class based on classifying the particular spectroscopic measurement.

BRIEF DESCRIPTION OF THE DRAWINGS

FIG. 10 is a flow chart of an example process for outlier removal and avoidance of false positive identification during spectroscopic classification.

DETAILED DESCRIPTION

Figure 1A:
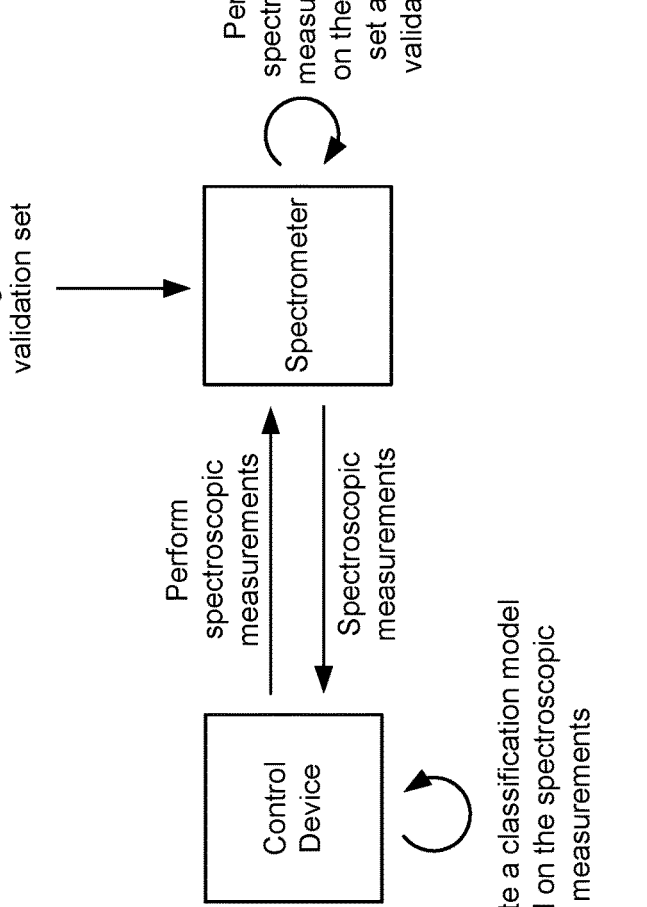
FIGS. 1A and 1B are diagrams of an overview of an example implementation described herein.

The following detailed description of example implementations refers to the accompanying drawings. The same reference numbers in different drawings may identify the same or similar elements.

Raw material identification (RMID) is a technique utilized to identify components (e.g., ingredients) of a particular sample for identification, verification, and/or the like. For example, RMID may be utilized to verify that ingredients in a pharmaceutical material correspond to a set of ingredients identified on a label. Similarly, raw material quantification is a technique utilized to perform a quantitative analysis on a particular sample, such as determining a concentration of a particular material in the particular sample. A spectrometer may be utilized to perform spectroscopy on a sample (e.g., the pharmaceutical material) to determine components of the sample, concentrations of components of the sample, and/or the like. The spectrometer may determine a set of measurements of the sample and may provide the set of measurements for a spectroscopic determination. A spectroscopic classification technique (e.g., a classifier) may facilitate determination of the components of the sample based on the set of measurements of the sample.

However, some unknown samples, which are to be subject to a spectroscopic classification, are not actually included in classes that a classification model is configured to classify. For example, for a classification model trained to distinguish between types of fish, a user may inadvertently provide beef for classification. In this case, a control device may perform a spectroscopic classification of the particular material, and may provide a false positive identification of the particular material as a particular type of fish, which would be inaccurate.

As another example, a classification model may be trained to classify types of sugar (e.g., glucose, fructose, galactose, and/or the like) and quantify respective concentrations of each type of sugar in unknown samples. However, a user of a spectrometer and a control device may inadvertently attempt to classify an unknown sample of sugar based on incorrectly using the spectrometer to perform a measurement. For example, the user may operate the spectrometer at an incorrect distance from the unknown sample, at environmental conditions different from calibration conditions at which spectroscopy was performed to train the classification model, and/or the like. In this case, the control device may receive an inaccurate spectrum for the unknown sample resulting in a false positive identification of the unknown sample as a first type of sugar at a first concentration, when the unknown sample is actually a second type of sugar at a second concentration.

Some implementations, described herein, may utilize a no-match class for a classification model to reduce false positive identification for spectroscopy. For example, a control device that receives a spectroscopic measurement of an unknown sample may determine whether to assign the unknown sample to a no-match class. In some implementations, the control device may determine that the unknown sample is to be assigned to the no-match class, and may provide information indicating that the unknown sample is assigned to the no-match class, thereby avoiding a false positive identification of the unknown sample. Alternatively, based on determining that the unknown sample is not to be assigned to the no-match class, the control device may analyze a spectrum of the unknown sample to provide a spectroscopic determination, such as of a classification, a concentration, and/or the like. Furthermore, the control device may utilize confidence metrics, such as probability estimates, decision values, and/or the like to filter out false positive identifications.

In this way, an accuracy of spectroscopy is improved relative to spectroscopy performed without use of a no-match class and/or confidence metrics. Moreover, a no-match class may be used when generating a classification model based on a training set of known spectroscopic samples. For example, a control device may determine that a sample, of the training set, is an outlier or not of a type corresponding to the rest of the training set (e.g., based on human error resulting in an incorrect sample being introduced into the training set), and may determine not to include data regarding the sample when generating a classification model, such as an in situ local classification model or may include the outlier in a no-match class for future training of the no-match class. An in situ local classification model may include a classification model generated by selecting a subset of classes, from the global classification model, with a highest confidence measure and generating a new model (e.g., the in situ local classification model) using only data from the selected subset of classes. In this case, generating an in situ local classification model increases prediction accuracy for a prediction performed using the in situ local classification model on an unknown sample relative to a prediction performed on the unknown sample using the global classification model. Further, when a classification model (e.g., the in situ local classification model), for which outlier detection and removal is performed, is evaluated to identify a classification of an unknown spectrum, an accuracy of the classification is improved relative to including the outlier spectrum in the classification model. In this way, the control device improves an accuracy of classification models for spectroscopy.

Figure 1B:
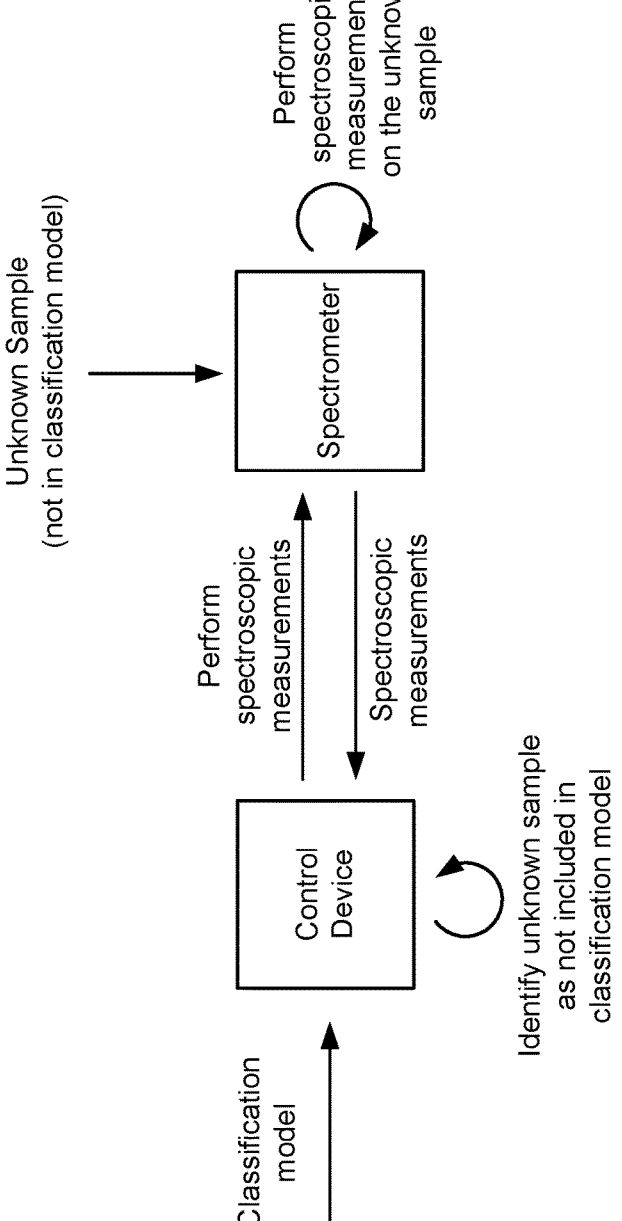

FIGS. 1A and 1B are diagrams of an overview of an example implementation 100 described herein. As shown in FIG. 1A, example implementation 100 may include a control device and a spectrometer.

As further shown in FIG. 1A, the control device may cause the spectrometer to perform a set of spectroscopic measurements on a training set and a validation set (e.g., a set of known samples utilized for training and validation of a classification model). The training set and the validation set may be selected to include a threshold quantity of samples for each class of the classification model. A class of the classification model may refer to a grouping of similar materials that share one or more characteristics in common, such as (in a pharmaceutical context) lactose materials, fructose materials, acetaminophen materials, ibuprophen materials, aspirin materials, and/or the like. Materials used to train the classification model, and for which raw material identification is to be performed using the classification model may be termed materials of interest.

As further shown in FIG. 1A, the spectrometer may perform the set of spectroscopic measurements on the training set and the validation set based on receiving an instruction from the control device. For example, the spectrometer may determine a spectrum for each sample of the training set and the validation set to enable the control device to generate a set of classes for classifying an unknown sample as one of the materials of interest for the classification model.

The spectrometer may provide the set of spectroscopic measurements to the control device. The control device may generate a classification model using a particular determination technique and based on the set of spectroscopic measurements. For example, the control device may generate a global classification model using a support vector machine (SVM) technique (e.g., a machine learning technique for information determination). The global classification model may include information associated with assigning a particular spectrum to a particular class of material of interest, and may include information associated with identifying a type of material of interest that is associated with the particular class. In this way, a control device can provide information identifying a type of material of an unknown sample based on assigning a spectrum of the unknown sample to a particular class.

In some implementations, the control device may receive spectra relating to samples for a no-match class. For example, the control device may receive spectra determined to be similar to spectra of the materials of interest, spectra relating to materials that may be confused for the materials of interest (e.g., visually, chemically, etc.), spectra relating to incorrect operation of the spectrometer (e.g., spectra of measurements performed without a sample, spectra of measurements performed at an incorrect distance between a sample and an optic of the spectrometer, etc.), and/or the like. Materials that are not materials of interest, and that may be included in the no-match class, may be termed nuisance materials or materials that are not of interest. In this case, the control device may generate the no-match class for the classification model, and may validate false positive identification avoidance using the no-match class based on spectra for nuisance materials included in the validation set. Additionally, or alternatively, during use of the classification model, the control device may receive information identifying a nuisance material, and may update the classification model to enable avoidance of false positive identification (e.g., identification of the nuisance material as one of the materials of interest).

As shown in FIG. 1B, the control device may receive the classification model (e.g., from storage, from another control device that generated the classification model, and/or the like). The control device may cause a spectrometer to perform a set of spectroscopic measurements on an unknown sample (e.g., an unknown sample for which classification or quantification is to be performed). The spectrometer may perform the set of spectroscopic measurements based on receiving an instruction from the control device. For example, the spectrometer may determine a spectrum for the unknown sample. The spectrometer may provide the set of spectroscopic measurements to the control device. The control device may attempt to classify the unknown sample based on the classification model, such as using a multi-stage classification technique.

With regard to FIG. 1B, the control device may attempt to determine whether the unknown sample is in the no-match class using the classification model. For example, the control device may determine a confidence metric corresponding to a likelihood that the unknown sample belongs to the no-match class. In this case, based on the control device determining that the confidence metric, such as a probability estimate, a decision value output of a support vector machine, and/or the like, satisfies a threshold, the control device may assign the unknown sample to the no-match class. In this case, the control device may report that the unknown sample cannot be accurately classified using the classification model, thereby reducing a likelihood that the unknown sample is subject to a false positive identification of the unknown sample as belonging to a class of a material of interest.

In some implementations, based on a first determination that the unknown sample does not belong to the no-match class, the control device may attempt to perform a determination of a particular sample of the unknown set using in situ local modeling. For example, the control device may determine a set of confidence metrics associated with the particular sample and the global classification model. In this case, the control device may select a subset of classes of the global classification model based on the one or more respective confidence metrics, and may generate a local classification model based on the set of classes. The local classification model may be an in situ classification model that is generated using the SVM technique and the subset of classes. Based on generating the in situ classification model, the control device may attempt to classify the unknown sample based on the local classification model. In this case, based on one or more confidence metrics associated with the local classification model satisfying a threshold, the control device may determine that the unknown sample does belong to the no-match class, and may report that the unknown sample cannot be classified using the classification model. Alternatively, the control device may determine that the unknown sample does not belong to the no-match class, and may report a classification relating to the unknown sample.

In this way, the control device enables spectroscopy for an unknown sample with improved accuracy relative to other classification models based on reducing a likelihood of reporting a false positive identification of the unknown sample as being a material of interest.

As indicated above, FIGS. 1A and 1B are provided merely as an example. Other examples are possible and may differ from what was described with regard to FIGS. 1A and 1B.

Figure 2:
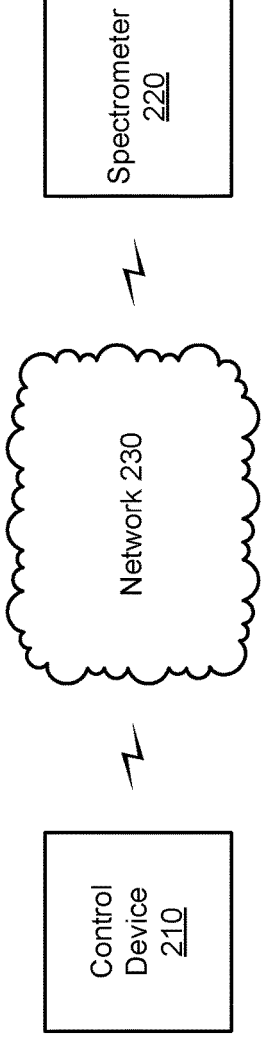
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a control device 210, a spectrometer 220, and a network 230. Devices of environment 200 may interconnect via wired connections, wireless connections, or a combination of wired and wireless connections.

Control device 210 may include one or more devices capable of storing, processing, and/or routing information associated with spectroscopic classification. For example, control device 210 may include a server, a computer, a wearable device, a cloud computing device, and/or the like that generates a classification model based on a set of measurements of a training set, validates the classification model based on a set of measurements of a validation set, and/or utilizes the classification model to perform spectroscopic classification based on a set of measurements of an unknown set. In some implementations, control device 210 may utilize a machine learning technique to determine whether a spectroscopic measurement of an unknown sample is to be classified into a no-match class to reduce a likelihood of a false positive identification, as described herein. In some implementations, control device 210 may be associated with a particular spectrometer 220. In some implementations, control device 210 may be associated with multiple spectrometers 220. In some implementations, control device 210 may receive information from and/or transmit information to another device in environment 200, such as spectrometer 220.

Spectrometer 220 may include one or more devices capable of performing a spectroscopic measurement on a sample. For example, spectrometer 220 may include a spectrometer device that performs spectroscopy (e.g., vibrational spectroscopy, such as a near infrared (NIR) spectrometer, a mid-infrared spectroscopy (mid-IR), Raman spectroscopy, and/or the like). In some implementations, spectrometer 220 may be incorporated into a wearable device, such as a wearable spectrometer and/or the like. In some implementations, spectrometer 220 may receive information from and/or transmit information to another device in environment 200, such as control device 210.

Network 230 may include one or more wired and/or wireless networks. For example, network 230 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although control device 210 and spectrometer 220 are described, herein, as being two separate devices, control device 210 and spectrometer 220 may be implemented within a single device. Additionally, or alternatively, a set of devices (e.g., one or more devices) of environment 200 may perform one or more functions described as being performed by another set of devices of environment 200.

Figure 3:
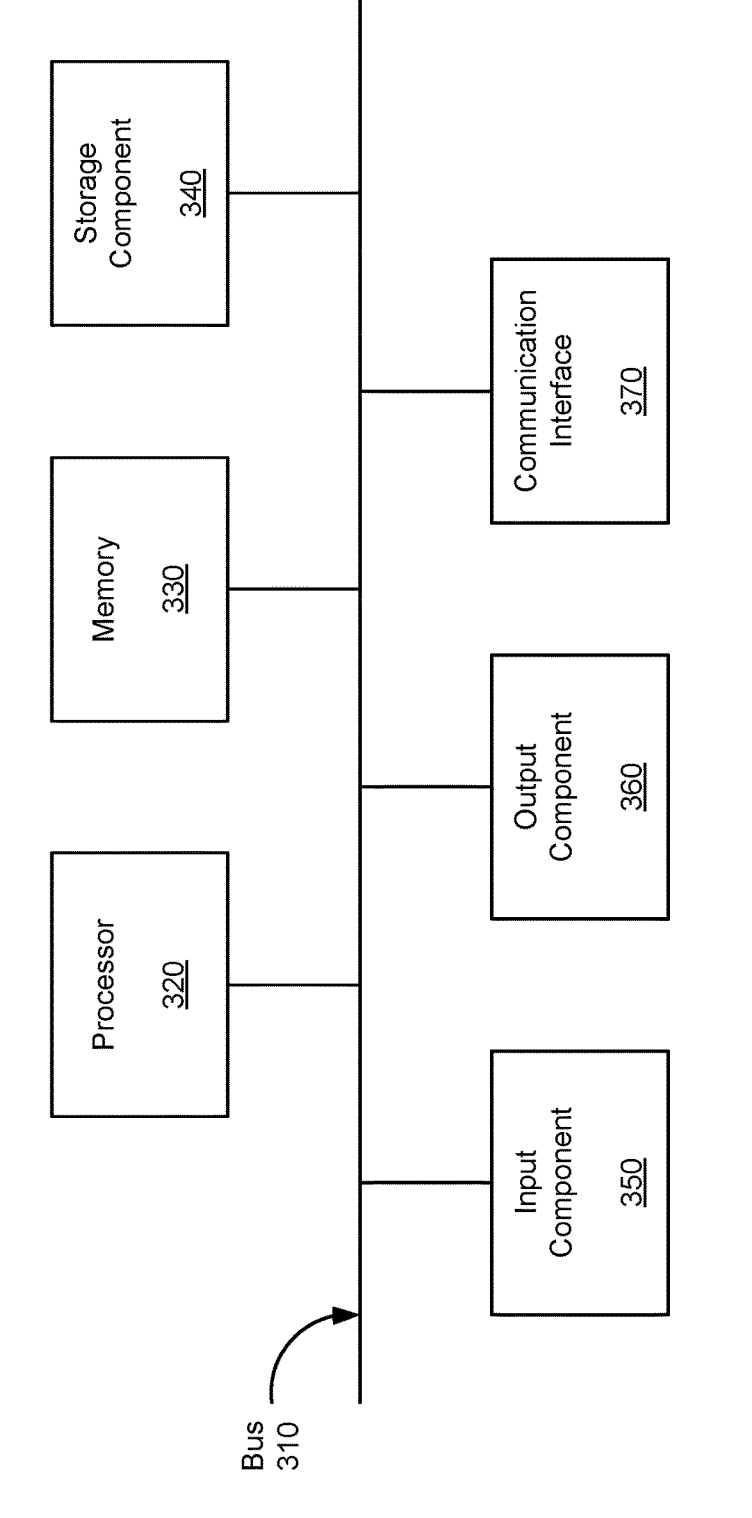
FIG. 3 is a diagram of example components of one or more devices of FIG. 2.

FIG. 3 is a diagram of example components of a device 300. Device 300 may correspond to control device 210 and/or spectrometer 220. In some implementations, control device 210 and/or spectrometer 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a wireless local area network interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
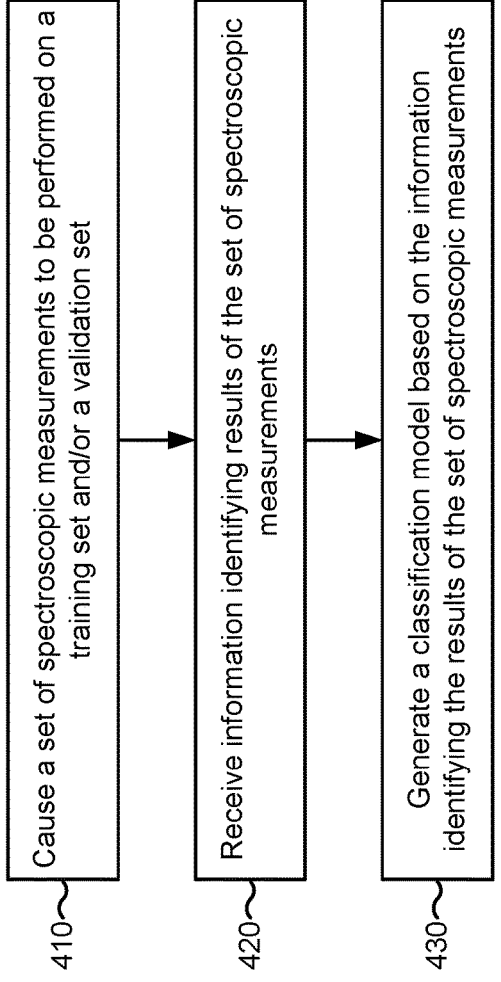
FIG. 4 is a flow chart of an example process for generating a classification model for spectroscopic classification.

FIG. 4 is a flow chart of an example process 400 for generating a classification model for spectroscopic classification. In some implementations, one or more process blocks of FIG. 4 may be performed by control device 210. In some implementations, one or more process blocks of FIG. 4 may be performed by another device or a group of devices separate from or including control device 210, such as spectrometer 220.

As shown in FIG. 4, process 400 may include causing a set of spectroscopic measurements to be performed on a training set and/or a validation set (block 410). For example, control device 210 may cause (e.g., using processor 320, communication interface 370, and/or the like) spectrometer 220 to perform a set of spectroscopic measurements on a training set and/or a validation set of samples to determine a spectrum for each sample of the training set and/or the validation set. The training set may refer to a set of samples of one or more known materials, which are utilized to generate a classification model. Similarly, the validation set may refer to a set of samples of one or more known materials, which are utilized to validate accuracy of the classification model. For example, the training set and/or the validation set may include one or more versions of a set of materials (e.g., one or more versions manufactured by different manufacturers to control for manufacturing differences).

In some implementations, the training set and/or the validation set may be selected based on an expected set of materials of interest for which spectroscopic classification is to be performed using the classification model. For example, when spectroscopic quantification is expected to be performed for pharmaceutical materials to determine a presence of a particular component of a pharmaceutical material, the training set and/or the validation set may include a set of samples of active pharmaceutical ingredients (APIs), excipients, and/or the like in a set of different possible concentrations.

In some implementations, the training set and/or the validation set may be selected to include a particular quantity of samples for each type of material. For example, the training set and/or the validation set may be selected to include multiple samples (e.g., 5 samples, 10 samples, 15 samples, 50 samples, etc.) of a particular material and/or concentration thereof. In some implementations, the quantity of samples may be less than a threshold. For example, a class for a homogeneous organic compound may be generated based on 50 spectra (e.g., spectroscopic scans) of 10 samples, 15 spectra of 3 samples, and/or the like. Similarly, for a heterogeneous organic compound, a class may be generated based on, for example, 100 spectra from 20 samples, 50 spectra from 10 samples, and/or the like. Similarly, a class for a biological or agricultural material may be generated based on 400 spectra from 40 samples, 200 spectra, from 20 samples, and/or the like. In some implementations, a quantity of samples and/or spectra that are used for a no-match class for a nuisance material may be associated with a same or a reduced quantity of samples and/or spectra as a non-no-match class for a same type of material (e.g., a homogenous organic compound, a heterogeneous organic compound, a biological or agricultural material, and/or the like). In this way, control device 210 can be provided with a threshold quantity of spectra associated with a particular type of material, thereby facilitating generation and/or validation of a class, for a classification model (e.g., a global classification model, a local classification model, etc.), to which unknown samples can be accurately assigned or a quantification model that may be used to quantify a spectra assigned to a class associated with the quantification model.

In some implementations, one or more samples of a material that is to be assigned to a no-match class may be included in the training set and/or the validation set. For example, spectrometer 220 may provide a measurement of a first material that is associated with a similar spectrum to a second material that is to be quantified using a quantification model. In this way, control device 210 may use machine learning to train avoidance of false positive identification. In some implementations, control device 210 may select materials for the no-match class based on received information. For example, control device 210 may receive information identifying nuisance materials with similar spectra, appearance, and/or the like to particular concentrations of a material of interest for which the classification model is to be generated. Additionally, or alternatively, control device 210 may perform a machine learning technique to automatically identify the nuisance materials for a particular material of interest. For example, control device 210 may use machine learning to perform pattern recognition to identify spectra of nuisance materials that are similar to spectra of materials of interest, to identify nuisance materials that appear visually similar to materials of interest, and/or the like.

In some implementations, control device 210 may cause baseline spectroscopic measurements to be performed to identify spectra for the no-match class. For example, control device 210 may cause a spectroscopic measurement to be performed without a sample present, with an incorrect background, with an incorrect illumination, and/or the like as baseline spectroscopic measurements to ensure that incorrect spectroscopic measurements are classified as the no-match class rather than classified as a particular material of interest. In this case, control device 210 may automatically control spectrometer 220, provide information using a user interface to instruct a user of spectrometer 220 to perform the incorrect measurements, and/or the like. Additionally, or alternatively, control device 210 may receive information indicating that a particular spectroscopic measurement was performed incorrectly to enable generation of the no-match class.

In some implementations, control device 210 may cause multiple spectrometers 220 to perform the set of spectroscopic measurements to account for one or more physical conditions. For example, control device 210 may cause a first spectrometer 220 and a second spectrometer 220 to perform a set of vibrational spectroscopic measurements using NIR spectroscopy. Additionally, or alternatively, control device 210 may cause the set of spectroscopic measurements to be performed at multiple times, in multiple locations, under multiple different laboratory conditions, and/or the like. In this way, control device 210 reduces a likelihood that a spectroscopic measurement is inaccurate as a result of a physical condition relative to causing the set of spectroscopic measurements to be performed by a single spectrometer 220.

As further shown in FIG. 4, process 400 may include receiving information identifying results of the set of spectroscopic measurements (block 420). For example, control device 210 may receive (e.g., using processor 320, communication interface 370, and/or the like) information identifying the results of the set of spectroscopic measurements. In some implementations, control device 210 may receive information identifying a set of spectra corresponding to samples of the training set and/or the validation set. For example, control device 210 may receive information identifying a particular spectrum, which was observed when spectrometer 220 performed spectroscopy on the training set. In some implementations, control device 210 may receive information identifying spectra for the training set and the validation set concurrently. In some implementations, control device 210 may receive information identifying spectra for the training set, may generate a classification model, and may receive information identifying spectra for the validation set after generating the classification model to enable testing of the classification model. In some implementations, control device 210 may receive other information as results of the set of spectroscopic measurements, such as information indicating that a measurement is performed inaccurately to generate a no-match class. Additionally, or alternatively, control device 210 may receive information associated with identifying an absorption of energy, an emission of energy, a scattering of energy, and/or the like.

In some implementations, control device 210 may receive the information identifying the results of the set of spectroscopic measurements from multiple spectrometers 220. For example, control device 210 may control for physical conditions, such as a difference between the multiple spectrometers 220, a potential difference in a lab condition, and/or the like, by receiving spectroscopic measurements performed by multiple spectrometers 220, performed at multiple different times, performed at multiple different locations, and/or the like.

In some implementations, control device 210 may remove one or more spectra from utilization in generating the classification model. For example, control device 210 may determine that the spectrum is an outlier spectrum and may remove the spectrum from a training set that may be used for an in situ local classification model used to perform a classification. In this way, control device 210 may improve an accuracy of classification models by reducing a likelihood that a classification model is generated or evaluated using incorrect, inaccurate, or outlier information regarding a training set or validation set.

As further shown in FIG. 4, process 400 may include generating a classification model based on the information identifying the results of the set of spectroscopic measurements (block 430). For example, control device 210 may generate (e.g., using processor 320, memory 330, storage component 340, and/or the like) a global classification model (e.g., for use in an in situ local modeling technique) associated with a principal component analysis (PCA)-SVM classifier technique based on the information identifying the results of the set of spectroscopic measurements.

In some implementations, control device 210 may perform a set of determinations to generate the global classification model. For example, control device 210 may generate a set of classes for a global classification model, and may assign a set of spectra, identified by the results of the set of spectroscopic measurements, into local classes based on using an SVM technique. In some implementations, during use of the global classification model, control device 210 identifies a threshold quantity of local classes corresponding to an unknown spectrum using confidence metrics relating to the global classification model, generates a local classification model based on the local classes, and determines an identity of the unknown spectrum based on the local classification model. In this case, the no-match class may be generated for the local classification model (e.g., the local classification model generated in situ from the global classification model may include a no-match class). In this way, by using in situ local modeling with a first classification and a second classification, control device 210 enables classification for large quantities of classes (e.g., greater than a threshold, such as greater than 50 classes, greater than 100 classes, greater than 200 classes, greater than 1000 classes, and/or the like). In some implementations, control device 210 may generate another type of classification model for classifying unknown spectra and/or use another type of classifier for the classification model. In some implementations, control device 210 may generate a classification model without generating a no-match class and/or without receiving training set samples representing the no-match class.

SVM may refer to a supervised learning model that performs pattern recognition and uses confidence metrics for classification. In some implementations, control device 210 may utilize a particular type of kernel function to determine a similarly of two or more inputs (e.g., spectra) when generating the global classification model using the SVM technique. For example, control device 210 may utilize a radial basis function (RBF) (e.g., termed SVM-rbf) type of kernel function, which may be represented as $k(x,y)=\exp(-\|x-y\|^2)$ for spectra x and y; a linear function (e.g., termed SVM-linear and termed hier-SVM-linear when utilized for a multi-stage determination technique) type of kernel function, which may be represented as $k(x,y)=<x \cdot y>$; a sigmoid function type of kernel function; a polynomial function type of kernel function; an exponential function type of kernel function; and/or the like.

In some implementations, control device 210 may utilize a particular type of confidence metric for SVM, such as a probability value based SVM (e.g., determination based on determining a probability that a sample is a member of a class of a set of classes), a decision value based SVM (e.g., determination utilizing a decision function to vote for a class, of a set of classes, as being the class of which the sample is a member), and/or the like. For example, during use of the classification model with decision value based SVM, control device 210 may determine whether an unknown sample is located within a boundary of a constituent class based on a plotting of a spectrum of the unknown sample, and may assign the sample to a class based on whether the unknown sample is located within the boundary of the constituent class. In this way, control device 210 may determine whether to assign an unknown spectrum to a particular class, to a no-match class, and/or the like.

In some implementations, control device 210 may utilize a particular class comparison technique for determining decision values. For example, control device 210 may utilize a one-versus-all technique (sometimes termed a one-versus-all others technique), where the classification model is divided into a group of sub-models with each sub-model being based on a class compared with each other class of the classification model, and the decision values being determined based on each sub-model. Additionally, or alternatively, control device 210 may utilize an all-pairs technique, where the classification model is divided into each possible pair of classes to form sub-models from which to determine decision values.

Although some implementations, described herein, are described in terms of a particular set of machine learning techniques, other techniques are possible for determining information regarding an unknown spectrum, such as a classification of the material and/or the like.

In some implementations, control device 210 may select the particular classifier that is to be utilized for generating the global classification model from a set of classification techniques. For example, control device 210 may generate multiple classification models corresponding to multiple classifiers and may test the multiple classification models, such as by determining a transferability of each model (e.g., an extent to which a classification model generated based on spectroscopic measurements performed on a first spectrometer 220 is accurate when applied to spectroscopic measurements performed on a second spectrometer 220), a large-scale determination accuracy (e.g., an accuracy with which a classification model can be utilized to concurrently classify a quantity of samples that satisfy a threshold), and/or the like. In this case, control device 210 may select a classifier, such as the SVM classifier (e.g., hier-SVM-linear), based on determining that the classifier is associated with superior transferability and/or large-scale determination accuracy relative to other classifiers.

In some implementations, control device 210 may generate the classification model based on information identifying samples of the training set. For example, control device 210 may utilize the information identifying the types or concentrations of materials represented by samples of the training set to identify classes of spectra with types or concentrations of materials. In some implementations, control device 210 may train the classification model when generating the classification model. For example, control device 210 may cause the model to be trained using a portion of the set of spectroscopic measurements (e.g., measurements relating to the training set). Additionally, or alternatively, control device 210 may perform an assessment of the classification model. For example, control device 210 may validate the classification model (e.g., for predictive strength) utilizing another portion of the set of spectroscopic measurements (e.g., the validation set).

In some implementations, control device 210 may validate the classification model using a multi-stage determination technique. For example, for in situ local modeling based classification, control device 210 may determine that a global classification model is accurate when utilized in association with one or more local classification models. In this way, control device 210 ensures that the classification model is generated with a threshold accuracy prior to providing the classification model for utilization, such as by control device 210, by other control devices 210 associated with other spectrometers 220, and/or the like.

In some implementations, control device 210 may provide the classification model to other control devices 210 associated with other spectrometers 220 after generating the classification model. For example, a first control device 210 may generate the classification model and may provide the classification model to a second control device 210 for utilization. In this case, for in situ local modeling based classification, the second control device 210 may store the classification model (e.g., a global classification model), and may utilize the classification model in generating one or more in situ local classification models for classifying one or more samples of an unknown set. Additionally, or alternatively, control device 210 may store the classification model for utilization by control device 210 in performing classification, in generating one or more local classification models (e.g., for in situ local modeling based classification), and/or the like. In this way, control device 210 provides the classification model for utilization in spectroscopic classification of unknown samples.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
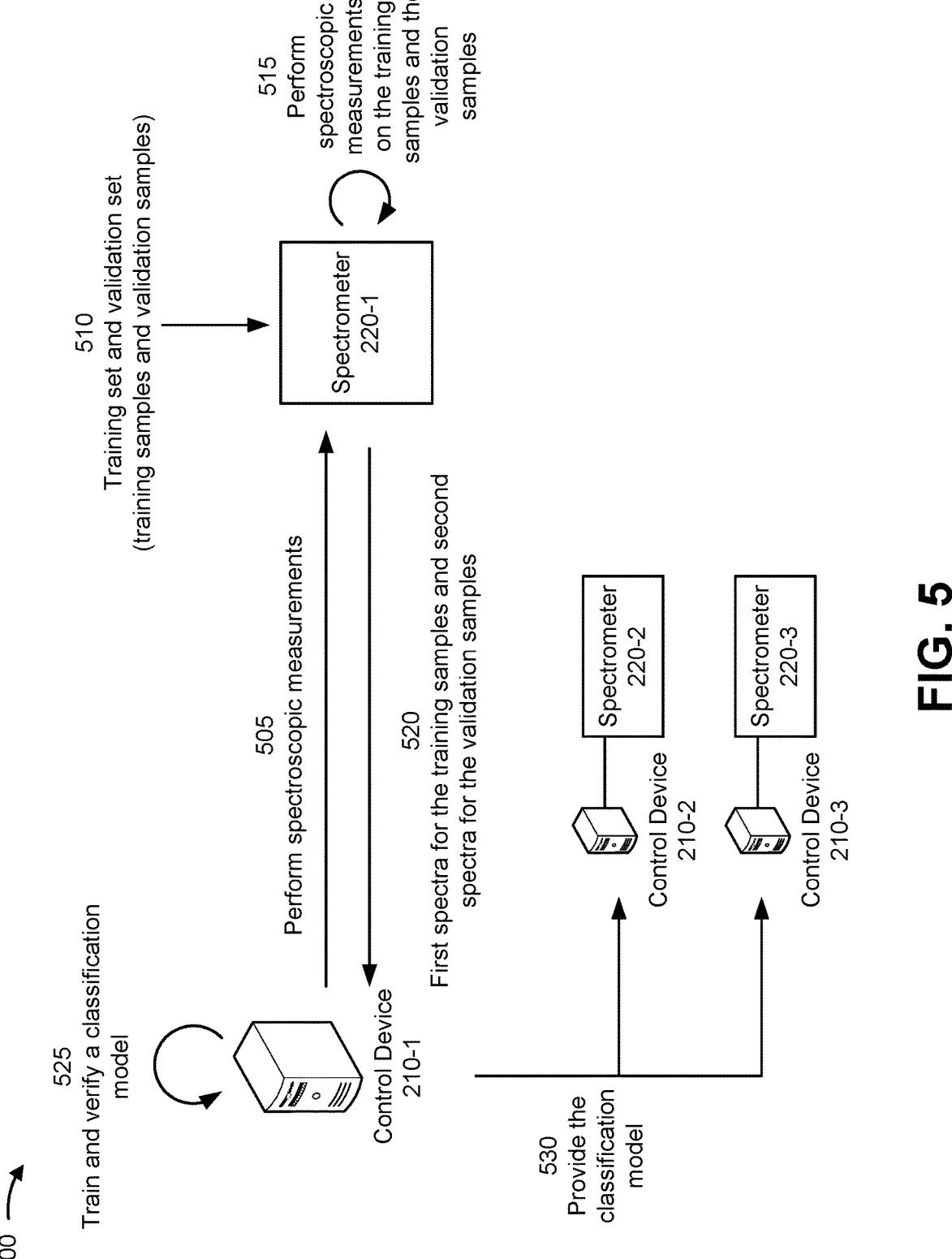
FIG. 5 is a diagram of an example implementation relating to the example process shown in FIG. 4.

FIG. 5 is a diagram of an example implementation 500 relating to example process 400 shown in FIG. 4. FIG. 5 shows an example of generating a classification model with false positive identification for quantification.

As shown in FIG. 5, and by reference number 505, control device 210-1 transmits information to spectrometer 220-1 to instruct spectrometer 220-1 to perform a set of spectroscopic measurements on training set and validation set 510. Assume that training set and validation set 510 includes a first set of training samples (e.g., measurements of which are utilized for training a classification model) and a second set of validation samples (e.g., measurements of which are utilized for validating accuracy of the classification model). As shown by reference number 515, spectrometer 220-1 performs the set of spectroscopic measurements based on receiving the instruction. As shown by reference number 520, control device 210-1 receives a first set of spectra for the training samples and a second set of spectra for the validation samples. In this case, the validation samples may include samples of multiple materials of interest for classification and one or more samples of one or more nuisance materials or incorrect measurements for training a no-match class for the classification model to avoid false positive identification. Assume that control device 210-1 stores information identifying each sample of training set and validation set 510.

With regard to FIG. 5, assume that control device 210-1 has selected to utilize a hier-SVM-linear classifier for generating the classification model (e.g., based on testing the hier-SVM-linear classifier against one or more other classifiers), which may be an in situ local modeling type of classification model. As shown by reference number 525, control device 210-1 trains the classification model using the hier-SVM-linear classifier and the first set of spectra and verifies the classification model using the hier-SVM-linear classifier and the second set of spectra. Control device 210-1 may generate a no-match class for the classification model using a subset of the first set of spectra to train the classification model to identify nuisance materials, and a subset of the second set of spectra to validate accuracy of the classification model in identifying the nuisance materials.

Assume that control device 210-1 determines that the classification model satisfies a validation threshold (e.g., has an accuracy that exceeds the validation threshold). As shown by reference number 530, control device 210-1 provides the classification model to control device 210-2 (e.g., for utilization when performing a classification on spectroscopic measurements performed by spectrometer 220-2) and to control device 210-3 (e.g., for utilization when performing a classification on spectroscopic measurements performed by spectrometer 220-3).

As indicated above, FIG. 5 is provided merely as an example. Other examples are possible and may differ from what was described with regard to FIG. 5.

In this way, control device 210 facilitates generation of a classification model based on a selected classification technique (e.g., selected based on model transferability, large-scale classification accuracy, and/or the like) and distribution of the classification model for utilization by one or more other control devices 210 associated with one or more spectrometers 220. Moreover, control device 210 improves an accuracy of the classification model by including spectroscopic measurements of nuisance materials to avoid false positive identification.

Figure 6:
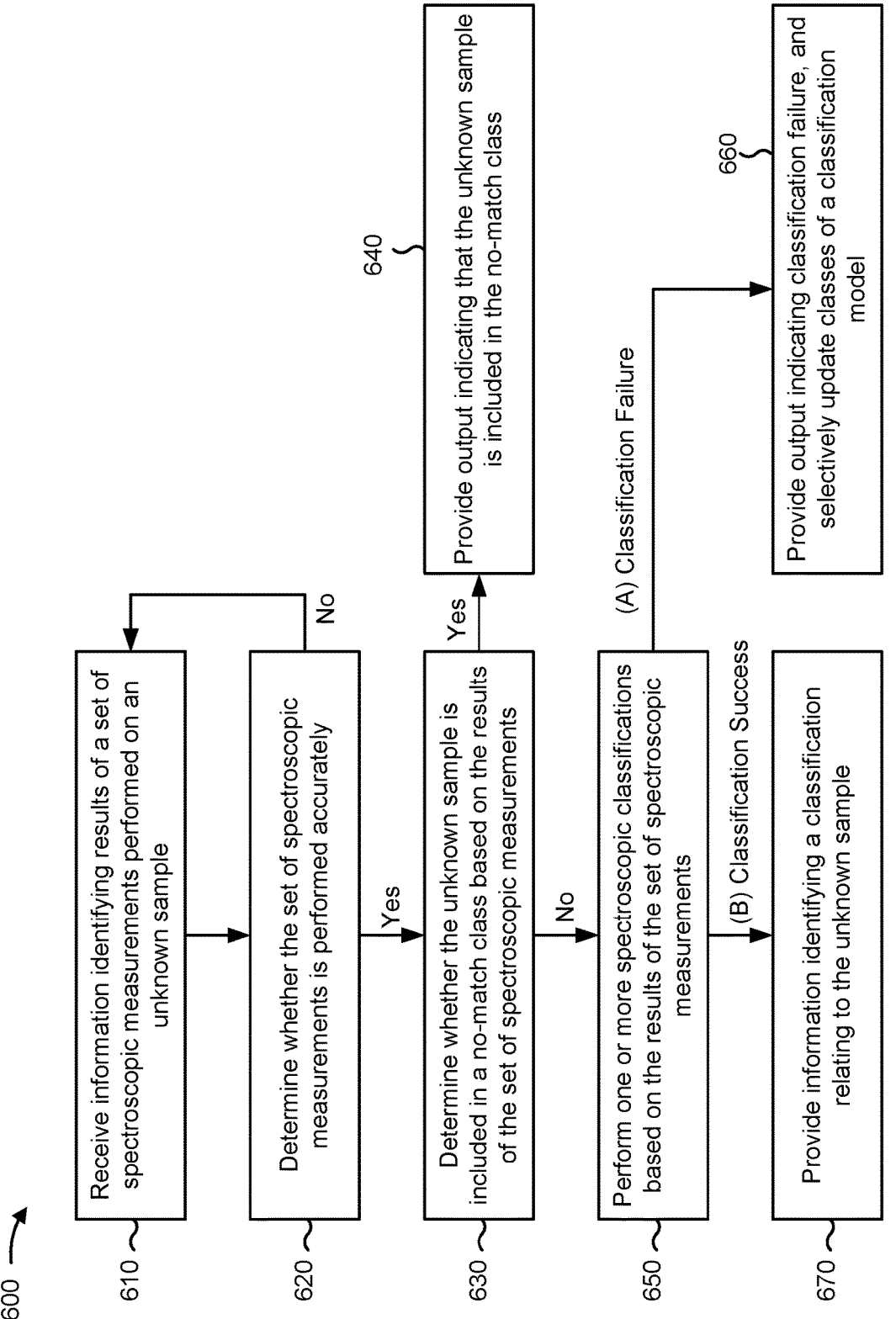
FIG. 6 is a flow chart of an example process for avoidance of false positive identification during spectroscopic classification.

FIG. 6 is a flow chart of an example process 600 for avoidance of false positive identification during raw material identification. In some implementations, one or more process blocks of FIG. 6 may be performed by control device 210. In some implementations, one or more process blocks of FIG. 6 may be performed by another device or a group of devices separate from or including control device 210, such as spectrometer 220.

As shown in FIG. 6, process 600 may include receiving information identifying results of a set of spectroscopic measurements performed on an unknown sample (block 610). For example, control device 210 may receive (e.g., using processor 320, communication interface 370, and/or the like) the information identifying the results of the set of spectroscopic measurements performed on the unknown sample. In some implementations, control device 210 may receive information identifying results of a set of spectroscopic measurements on an unknown set (e.g., of multiple samples). The unknown set may include a set of samples (e.g., unknown samples) for which a determination (e.g., a spectroscopic classification) is to be performed. For example, control device 210 may cause spectrometer 220 to perform the set of spectroscopic measurements on the set of unknown samples, and may receive information identifying a set of spectra corresponding to the set of unknown samples.

In some implementations, control device 210 may receive the information identifying the results from multiple spectrometers 220. For example, control device 210 may cause multiple spectrometers 220 to perform the set of spectroscopic measurements on the unknown set (e.g., the same set of samples), and may receive information identifying a set of spectra corresponding to samples of the unknown set. Additionally, or alternatively, control device 210 may receive information identifying results of a set of spectroscopic measurements performed at multiple times, in multiple locations, and/or the like, and may classify and/or quantify a particular sample based on the set of spectroscopic measurements performed at the multiple times, in the multiple locations, and/or the like (e.g., based on averaging the set of spectroscopic measurements or based on another technique). In this way, control device 210 may account for physical conditions that may affect results of the set of spectroscopic measurements.

Additionally, or alternatively, control device 210 may cause a first spectrometer 220 to perform a first portion of the set of spectroscopic measurements on a first portion of the unknown set and may cause a second spectrometer 220 to perform a second portion of the set of spectroscopic measurements on a second portion of the unknown set. In this way, control device 210 may reduce a quantity of time to perform the set of spectroscopic measurements relative to causing all the spectroscopic measurements to be performed by a single spectrometer 220.

As further shown in FIG. 6, process 600 may include determining whether the set of spectroscopic measurements is performed accurately (block 620). For example, control device 210 may determine (e.g., using processor 320, memory 330, storage component 340, and/or the like) whether the set of spectroscopic measurements is performed accurately. In some implementations, control device 210 may determine whether a spectroscopic measurement of an unknown sample was performed at a calibrated distance (e.g., between an optic component of spectrometer 220 and the sample, between an optic component of spectrometer 220 and a background to the sample, and/or the like). Additionally, or alternatively, control device 210 may determine whether a spectroscopic measurement of the unknown sample was performed at a calibrated temperature, at a calibrated pressure, at a calibrated humidity, using a calibrated background, using a calibrated spectrometer, and/or the like.

The calibrated values for calibration conditions, such as the calibrated distance, the calibrated temperature, the calibrated pressure, the calibrated humidity, the calibrated background, and/or the like, may include a value at which the model was trained and/or validated. For example, control device 210 may receive measurement data from spectrometer 220 identifying values for measurement conditions, such as a temperature, a distance between the unknown sample and an optic component of spectrometer 220, and/or the like, and control device 210 may verify that the model was trained using a training set and/or validation set associated with calibration values for calibration conditions within a threshold amount of the values.

Additionally, or alternatively, control device 210 may perform a sanity check using a single class SVM (SC-SVM) classifier technique or a median absolute deviation (MAD), among other outlier detection schemes, to determine whether an unknown spectrum is associated with a correctly performed measurement. For example, control device 210 may aggregate multiple classes in the classification model to form an aggregated classification model with a single class and use an SVM classifier with decision values to determine whether an unknown sample is an outlier sample. In this case, when the unknown sample is an outlier sample, control device 210 may determine that the set of spectroscopic measurements is not performed accurately, and may cause the set of spectroscopic measurements to be performed again, and may receive another set of results identifying another set of spectroscopic measurements (block 620— NO). In this way, control device 210 enables identification of unknown spectra differing from the classification model by a threshold amount without having the classification model trained using samples similar to the unknown sample (e.g., also differing from training set samples of the material of interest by the threshold amount). Moreover, control device 210 reduces an amount of samples to be collected for generating the classification model, thereby reducing cost, time, and computing resource utilization (e.g., processing resources and memory resources) relative to obtaining, storing, and processing other samples for nuisance materials differing from the material of interest by the threshold amount.

Furthermore, control device 210 reduces a likelihood of an inaccurate result of spectroscopy (e.g., an inaccurate quantification, an inaccurate determination, and/or the like) relative to performing spectroscopy without determining whether measurement conditions match calibration conditions. Moreover, based on determining that the measurements of the unknown sample were performed correctly before attempting to classify the unknown sample, control device 210 reduces a utilization of computing resources relative to attempting to perform spectroscopy, failing as a result of incorrect measurement, and performing another attempt at spectroscopy.

As further shown in FIG. 6, based on determining that the set of spectroscopic measurements is performed accurately (block 620—YES) process 600 may include determining whether the unknown sample is included in a no-match class based on the results of the set of spectroscopic measurements (block 630). For example, control device 210 may attempt to determine (e.g., using processor 320, memory 330, storage component 340, and/or the like) whether the unknown sample is to be classified into the no-match class (e.g., a material that is not of interest or a nuisance material). In some implementations, control device 210 may classify the unknown sample to determine whether the unknown sample is included in the no-match class. For example, control device 210 may use an SVM-rbf kernel function or SVM-linear kernel function for a model to determine a decision value for classifying the unknown sample into the no-match class. Based on the decision value satisfying a threshold decision value, control device 210 may determine that the unknown sample belongs to the no-match class (e.g., the unknown sample is determined to be a nuisance material, the spectra is determined to be associated with a baseline spectroscopic measurement, such as a measurement performed using an incorrect measurement distance, a measurement performed using an incorrect measurement background, a measurement performed using an incorrect measurement illumination, a measurement performed without a sample present, and/or the like). In this way, control device 210 determines that a classification model for spectroscopy is not calibrated for use with a spectrum of a particular unknown sample, and avoids a false positive identification of the particular unknown sample. Alternatively, control device 210 may determine that the unknown sample does not belong to the no-match class.

As further shown in FIG. 6, based on determining that the unknown sample is included in the no-match class (block 630—YES), process 600 may include providing output indicating that the unknown sample is included in the no-match class (block 640). For example, control device 210 may provide (e.g., using processor 320, memory 330, storage component 340, communication interface 370, and/or the like) information, such as via a user interface, indicating that the unknown sample is included in the no-match class. In some implementations, control device 210 may provide information associated with identifying the unknown sample. For example, based on attempting to quantify an amount of a particular chemical in a particular plant, and determining that an unknown sample is not of the particular plant (but, instead, of another plant, such as based on human error), control device 210 may provide information identifying the other plant. In some implementations, control device 210 may obtain another classification model, and may use the other classification model to identify the unknown sample based on assigning the unknown spectrum to the no-match class of the classification model.

In this way, control device 210 reduces a likelihood of providing incorrect information based on a false positive identification of the unknown sample, and enables error correction by a technician by providing information to assist in determining that the unknown sample was of the other plant rather than the particular plant.

As further shown in FIG. 6, based on determining that the unknown sample is not included in the no-match class (block 630—NO) process 600 may include performing one or more spectroscopic determinations based on the results of the set of spectroscopic measurements (block 650). For example, control device 210 may perform (e.g., using processor 320, memory 330, storage component 340, and/or the like) one or more spectroscopic determinations based on the results of the set of spectroscopic measurements. In some implementations, control device 210 may assign the unknown sample to a particular class, of a set of classes of the global classification model, to perform a first determination. For example, control device 210 may determine that a particular spectrum associated with the particular sample corresponds to a local class of materials (e.g., cellulose materials, lactose materials, caffeine materials, etc.) based on a global classification model.

In some implementations, control device 210 may assign the particular sample based on a confidence metric. For example, control device 210 may determine, based on a global classification model, a probability that a particular spectrum is associated with each class of the global classification model. In this case, control device 210 may assign the unknown sample to the particular local class based on a particular probability for the particular local class exceeding other probabilities associated with other, non-local classes. In this way, control device 210 determines a type of material that the sample is associated with, thereby identifying the sample. In some implementations, control device 210 may determine that the unknown sample does not satisfy a threshold associated with any class and does not satisfy a threshold associated with the no-match class. In this case, control device 210 may provide output indicating that the unknown sample is not included in any of the classes and cannot be assigned to the no-match class with a level of confidence corresponding to the threshold associated with the no-match class.

In some implementations, to perform in situ local modeling, such as for classification models with greater than a threshold quantity of classes, control device 210 may generate a local classification model based on the first determination. The local classification model may refer to an in situ classification model generated using an SVM determination technique (e.g., SVM-rbf, SVM-linear, etc. kernel functions;

probability value based SVM, decision value based SVM, etc.; and/or the like) based on confidence metrics associated with the first determination. In some implementations, control device 210 may generate multiple local classification models.

In some implementations, control device 210 may generate a local quantification model based on performing the first determination using the global classification model. For example, when control device 210 is being utilized to determine a concentration of a substance in an unknown sample, and multiple unknown samples are associated with different quantification models for determining the concentration of the substance, control device 210 may utilize the first determination to select a subset of classes as local classes for the unknown sample and generate a local classification model with which control device 210 can classify (a second determination) the unknown sample and select (based on the second determination) a quantification model for the unknown sample based on a result of the first determination (and the subsequent second determination). In this way, control device 210 utilizes hierarchical determination and quantification models to improve spectroscopic classification.

In some implementations, control device 210 may perform the second determination based on the results and the local classification model. For example, control device 210 may classify the unknown sample as one of the materials of interest for the global classification model based on the local classification model and the particular spectrum. In some implementations, control device 210 may determine a set of confidence metrics associated with the particular spectrum and the local classification model. For example, control device 210 may determine a probability that the particular spectrum is associated with each class of the local classification model, and may assign the particular spectrum (e.g., the unknown sample associated with the particular spectrum) to a class with a higher probability than other classes of the local classification model. In this way, control device 210 identifies an unknown sample. In some implementations, control device 210 may determine that a no-match class for the local classification model, and may assign the particular spectrum to the no-match class for the local classification model. In some implementations, control device 210 may determine that the unknown sample fails to satisfy a threshold confidence metric for the classes of the classification model, and may determine a classification failure for the unknown sample. In this way, based on using a threshold confidence metric, control device 210 reduces a likelihood of a false positive identification of the unknown sample.

In some implementations, control device 210 may perform a quantification after performing the first determination (and/or after performing the second determination). For example, control device 210 may select a local quantification model based on performing one or more determinations, and may perform a quantification relating to the particular sample based on selecting the local quantification model. As an example, when performing raw material identification to determine a concentration of a particular chemical in a plant material, where the plant material is associated with multiple quantification models (e.g., relating to whether the plant is grown indoors or outdoors, in winter or in summer, and/or the like), control device 210 may perform a set of determinations to identify a particular quantification model. In this case, the control device 210 may determine that the plant is grown indoors in winter based on performing a set of determinations, and may select a quantification model relating to the plant being grown indoors in winter for determining the concentration of the particular chemical.

As further shown in FIG. 6, based on a classification failure when performing the one or more spectroscopic classification (block 650—A), process 600 may include providing output indicating the classification failure, and selectively updating classes of a classification model (block 660). For example, control device 210 may provide (e.g., using processor 320, memory 330, storage component 340, communication interface 370, and/or the like) information indicating the classification failure. For example, based on determining that a confidence level associated with the classification does not satisfy a threshold confidence level, control device 210 may provide an output indicating a classification failure, thereby reducing a likelihood of a false-positive determination. Additionally, or alternatively, based on determining that the confidence level does not satisfy the threshold, control device 210 may selectively update classes of the classification model for performing the classification. For example, control device 210 may obtain additional information (e.g., such as from an operator, a database, and/or the like) identifying the sample, and may determine that the sample belongs to a labeled class. In this case, control device 210 may update the labeled classes to enable improved subsequent spectroscopic classification. Additionally, or alternatively, control device 210 may obtain information indicating that the sample does not belong to a labeled class. In this case, control device 210 may update the no-match class to enable improved subsequent no-match classification. In this way, control device 210 enabled iterative model enhancement for spectroscopic classification.

As further shown in FIG. 6, based on a classification success when performing the one or more spectroscopic classification (block 650—B), process 600 may include providing information identifying a classification relating to the unknown sample (block 670). For example, control device 210 may provide (e.g., using processor 320, memory 330, storage component 340, communication interface 370, and/or the like) information identifying a classification relating to the unknown sample. In some implementations, control device 210 may provide information identifying a particular class for the unknown sample. For example, control device 210 may provide information indicating that a particular spectrum associated with the unknown sample is determined to be associated with the particular class, thereby identifying the unknown sample.

In some implementations, control device 210 may provide information indicating a confidence metric associated with assigning the unknown sample to the particular class. For example, control device 210 may provide information identifying a probability that the unknown sample is associated with the particular class and/or the like. In this way, control device 210 provides information indicating a likelihood that the particular spectrum was accurately assigned to the particular class.

In some implementations, control device 210 may provide a quantification based on performing a set of classifications. For example, based on identifying a local quantification model relating to a class of the unknown sample, control device 210 may provide information identifying a concentration of a substance in an unknown sample. In some implementations, control device 210 may update the classification model based on performing a set of classifications. For example, control device 210 may generate a new classification model including the unknown sample as a sample of the training set based on determining a classification of the unknown sample as a material of interest, as a nuisance material, and/or the like.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7A:
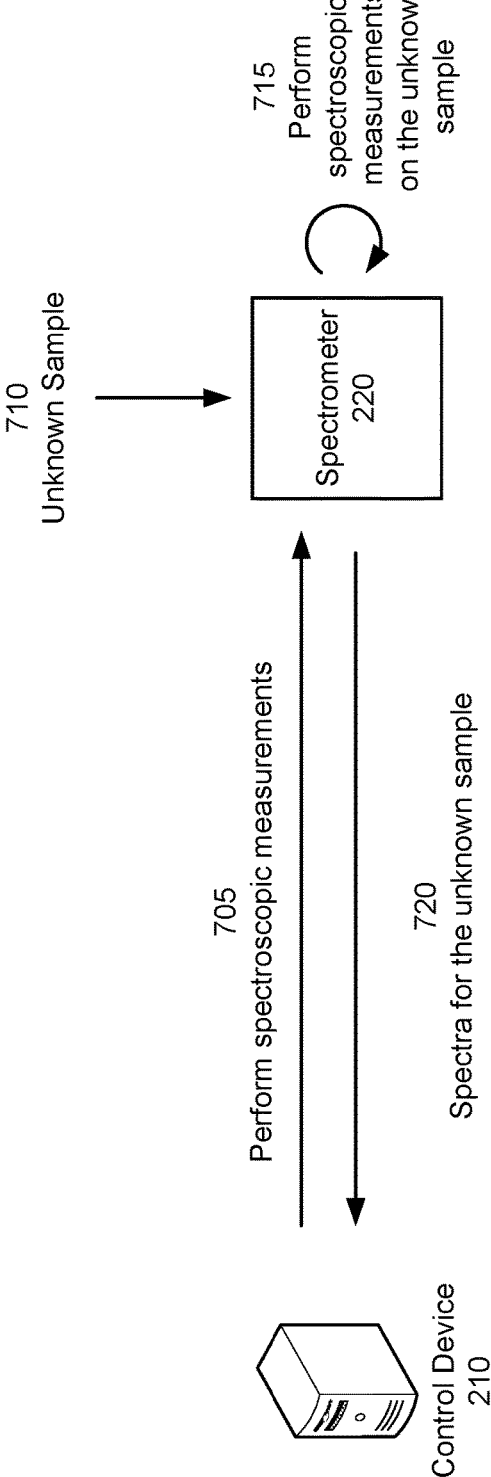
FIGS. 7A and 7B are diagrams of an example implementation relating to the example process shown in FIG. 6.
Figure 7B:
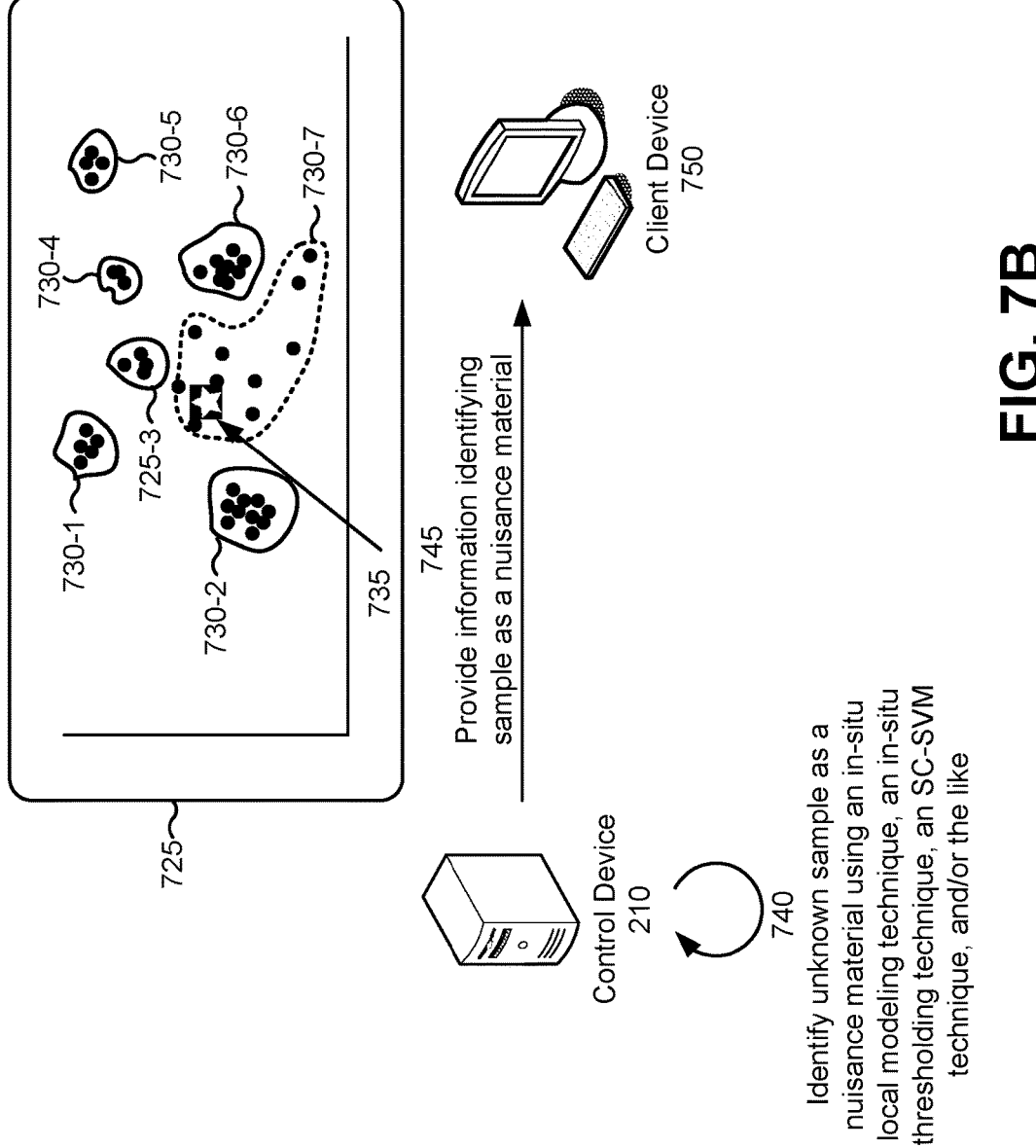

FIGS. 7A and 7B are diagrams of an example implementation 700 relating to prediction success rates associated with example process 600 shown in FIG. 6. FIGS. 7A and 7B show example results of raw material identification using a hierarchical support vector machine (hier-SVM-linear) based technique.

As shown in FIG. 7A, and by reference number 705, control device 210 may cause spectrometer 220 to perform a set of spectroscopic measurements. For example, control device 210 may provide an instruction to cause spectrometer 220 to obtain a spectrum for an unknown sample to determine a classification of the unknown sample as a particular material of interest of a set of materials of interest that a classification model is trained to identify. As shown by reference number 710 and reference number 715, spectrometer 220 may receive the unknown sample and may perform the set of spectroscopic measurements on the unknown sample. As shown by reference number 720, control device 210 may receive spectra for the unknown sample based on spectrometer 220 performing the set of spectroscopic measurements on the unknown sample.

As shown in FIG. 7B, control device 210 may use a classification model 725 to perform spectroscopic classification. Classification model 725 includes a set of classes 730 identified for a set of spectra of a training set. For example, classification model 725 includes classes 730-1 through 730-6 of potential materials of interest and a no-match class 730-7 of nuisance materials (e.g., similar materials; similar spectra; incorrectly obtained spectra, such as incorrect illumination spectra, incorrect distance spectra, incorrect background spectra, etc.; and/or the like).

As further shown in FIG. 7B, and by reference numbers 735 and 740, a spectrum of the unknown sample is assigned to the no-match class, and the unknown sample is identified as a nuisance material (e.g., a member of the no-match class). For example, control device 210 may use an in situ local modeling technique to generate a local model based on a global model (e.g., classification model 725), and may determine whether the unknown sample is a nuisance material based on the local model. In some implementations, control device 210 may perform an in situ thresholding technique to determine whether the unknown sample is a nuisance material. For example, control device 210 may self-validate or cross-validate decision values associated with a first most likely class of the unknown sample and/or a runner up class of the sample (e.g., a second most likely class), and may use the decision values to set an upper bound and lower bound for a prediction threshold. In some implementations, control device 210 may utilize multiple local modeling strategies. For example, control device 210 may utilize a first modeling technique to determine a winner class and a second modeling technique to determine a confidence metric. In some implementations, control device 210 may utilize a single class SVM (SC-SVM) technique to determine whether the unknown sample is a nuisance material. As shown by reference number 745, control device 210 provides output to client device 750 indicating that the unknown sample is a nuisance material, rather than providing a false positive identification of the unknown sample as a particular concentration of one of the materials of interest.

As indicated above, FIGS. 7A and 7B are provided merely as an example. Other examples are possible and may differ from what was described with regard to FIGS. 7A and 7B.

Figure 8:
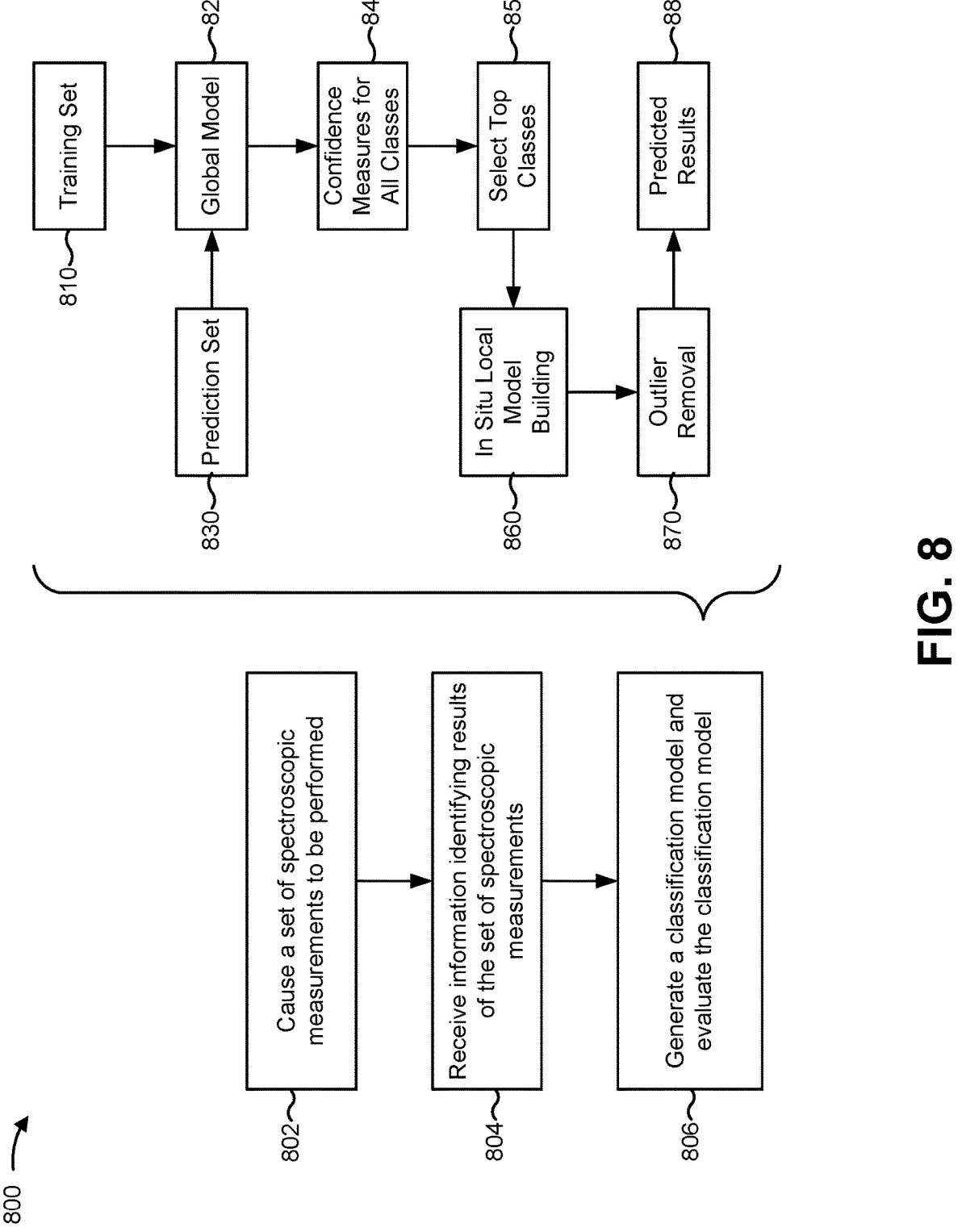
FIG. 8 is a flow chart of an example process for outlier removal and avoidance of false positive identification during spectroscopic classification.

FIG. 8 is a flow chart of an example process 800 for generating and evaluating a classification model for spectroscopic classification. In some implementations, one or more process blocks of FIG. 8 may be performed by control device 210. In some implementations, one or more process blocks of FIG. 8 may be performed by another device or a group of devices separate from or including control device 210, such as spectrometer 220.

As shown in FIG. 8, process 800 may include causing a set of spectroscopic measurements to be performed (block 802). For example, control device 210 may cause (e.g., using processor 320, communication interface 370, and/or the like) spectrometer 220 to perform a set of spectroscopic measurements on a training set and/or a validation set of samples to determine a spectrum for each sample of the training set and/or the validation set, as described in more detail above.

As further shown in FIG. 8, process 800 may include receiving information identifying results of the set of spectroscopic measurements (block 804). For example, control device 210 may receive (e.g., using processor 320, communication interface 370, and/or the like) information identifying the results of the set of spectroscopic measurements, as described in more detail above.

As further shown in FIG. 8, process 800 may include generating a classification model and evaluate the classification model (block 806). For example, control device 210 may generate (e.g., using processor 320, memory 330, storage component 340, and/or the like) a global classification model, as described in more detail above, and a local classification model (e.g., using an in situ local modeling technique as described in more detail above) and evaluate the global classification model and the local classification model to generate a prediction.

For example, control device 210 may using a training set to train a global classification model and use the global classification model to perform a first evaluation of a prediction set (blocks 810-830). Based on evaluating the prediction set, control device 210 may generate a set of confidence measures for each class of the global classification model (block 840). Control device 210 may select a subset of classes from the global classification model for in situ local model building (block 850). For example, control device 210 may select a subset of classes with a highest set of confidence measures as 'Top Classes' from the global classification model and may use the 'Top Classes' for in situ local model building of a local classification model (block 860).

In some implementations, control device 210 may perform an outlier removal procedure in connection with the local classification model (block 870). For example, control device 210 may evaluate the subset of classes and/or one or more local classification models generated therefrom to identify one or more outlier spectra. In this case, control device 210 may remove data relating to the one or more outlier spectra from the subset of classes and/or the one or more local classification models generated therefrom. In this way, by removing the one or more outlier spectra, a prediction threshold associated with preventing false positive samples from triggering false positive predictions may be increased (improved) without compromising a predictive accuracy, thereby improving an overall accuracy of predictions performed using the one or more local classification models (block 880).

In some implementations, control device 210 may use a particular technique for outlier removal. For example, control device 210 may perform a median absolute deviation (MAD) procedure to remove outliers from the subset of classes and/or the one or more local classification models generated therefrom. In the MAD procedure, control device 210 may determine a median spectrum of all spectra in a targeted class, calculate a MAD value based on a median of absolute values of deviations of all spectra in the target class from the median spectra, calculate a MAD factor for each spectrum of interest based at least in part on the absolute value of a deviation of a spectrum from a median spectrum divided by the MAD value, and determine whether the MAD factor is greater than a threshold amount. In this case, when a spectrum is greater than a threshold MADs from a median value in multi-variate space (e.g., the MAD factor is greater than the threshold amount), control device 210 may classify the spectrum as an outlier and remove the spectrum from data used in performing predictions on the prediction set. Additionally, or alternatively, control device 210 may use a Grubb's test (also termed a maximum normalized residual test or extreme studentized deviate test) based technique, a Mahalanobis distance based technique, or a Hotelling's T-Squared distribution based technique, among other possible techniques, for outlier removal. In this case, control device 210 may iteratively detect outlier spectra and remove the outlier spectra from the data used in performing predictions on the prediction set.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

Figure 9A:
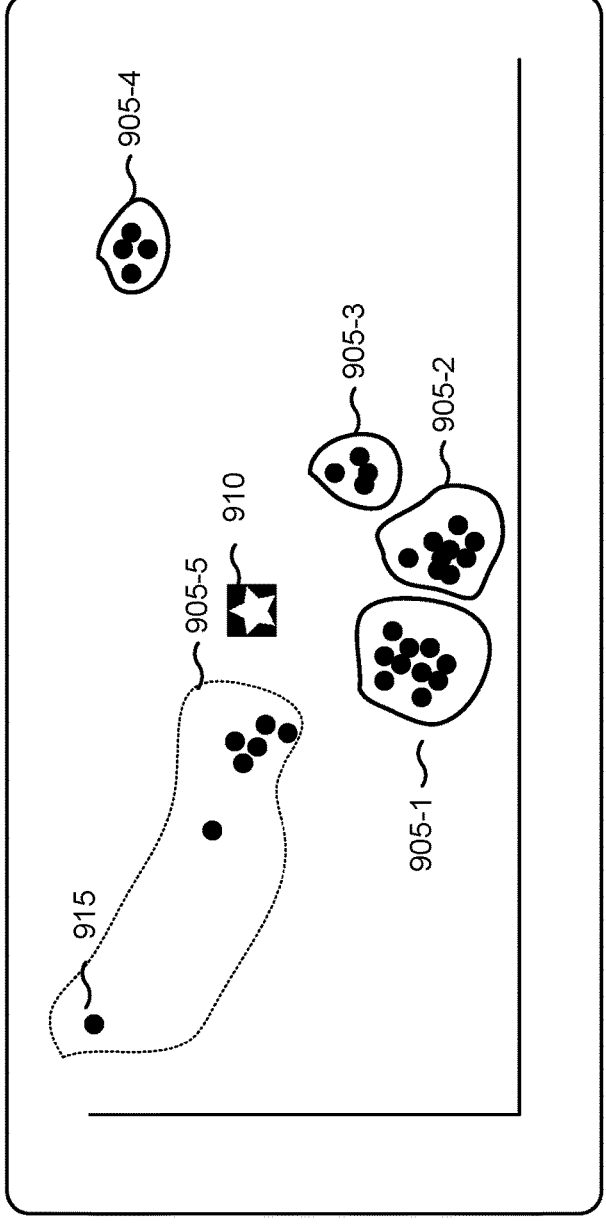
FIGS. 9A and 9B are diagrams of an example implementation relating to the example process shown in FIG. 8.
Figure 9B:
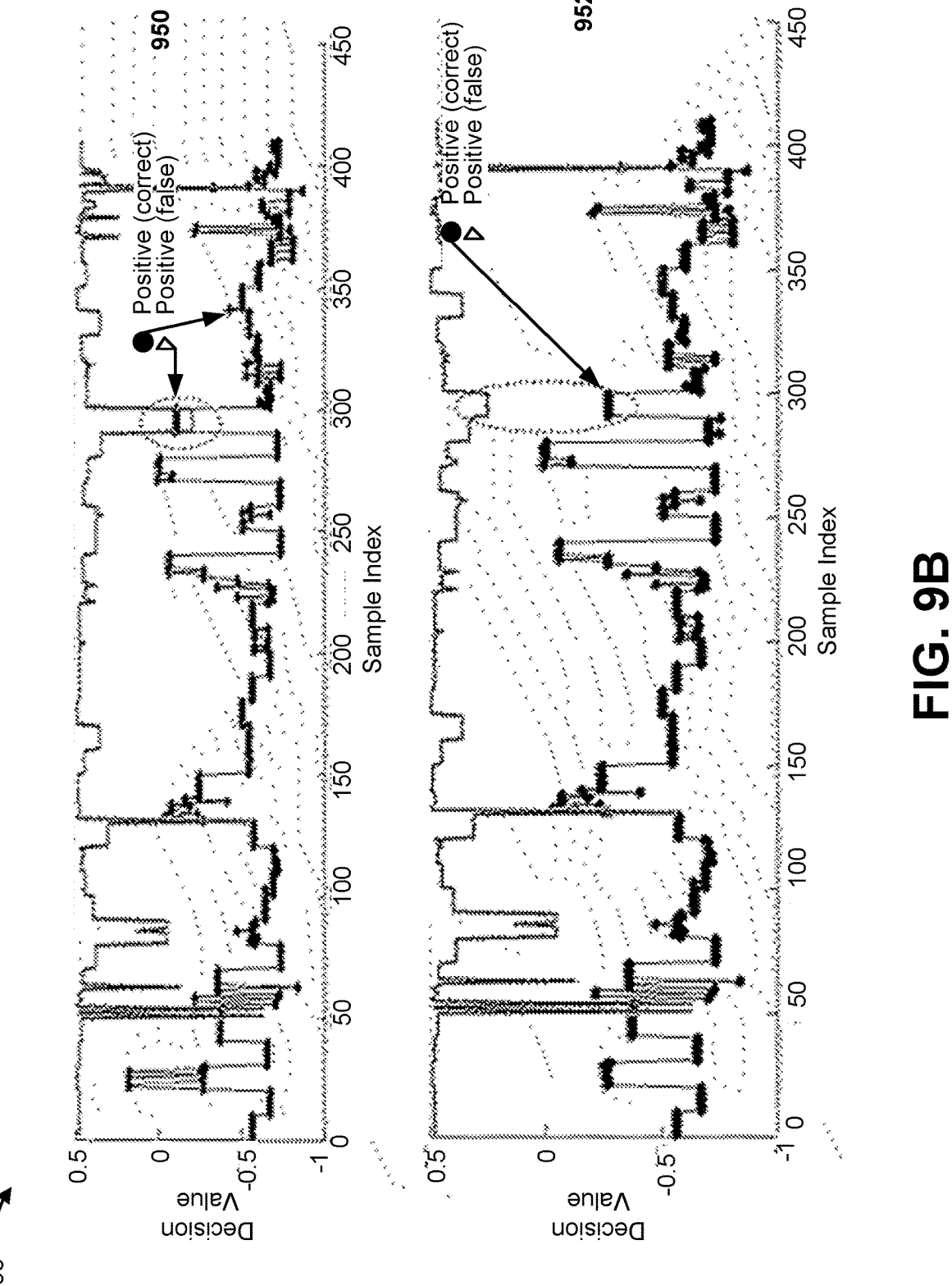

FIGS. 9A and 9B are diagrams of an example implementation 900 relating to outlier removal associated with example process 800 shown in FIG. 8. FIGS. 9A and 9B show example results of raw material identification using a hierarchical support vector machine (hier-SVM-linear) based technique with outlier removal.

As shown in FIG. 9A, a control device 210 may generate a local model for a set of samples of a prediction set. In this case, the local model corresponds to samples 291-300 of the prediction set of FIG. 9B. The local model includes a set of classes 905, which are to be used for prediction of samples 910. As shown by reference number 915, control device 210 may identify a spectrum of class 905-5 as an outlier spectrum. In this case, control device 210 determines that the spectrum is an outlier spectrum for class 905-5. Additionally, or alternatively, control device 210 may determine that the spectrum is an outlier spectrum for all classes 905. In this case, a presence of the outlier spectrum in class 905-5 may result in a prediction confidence measure failing to satisfy a prediction threshold for performing an accurate classification. For example, as shown in FIG. 9B and by diagram 950, samples 291-300 result in a false positive prediction. In contrast, after removal of the outlier spectrum, as shown by diagram 952, samples 291-300 result in a correct positive prediction. In some implementations, the prediction threshold may be based on an SVM technique. For example, control device 210 may use the SVM technique to set the prediction threshold for determining whether to classify a spectrum in a particular class. In this way, removal of outlier spectrum from, for example, an in situ local classification model improves a predictive accuracy of classifications performed using the in situ local classification model.

As indicated above, FIGS. 9A and 9B are provided merely as an example. Other examples are possible and may differ from what was described with regard to FIGS. 9A and 9B.

FIG. 10 is a flowchart of an example process 1000 associated with outlier removal and avoidance of false positive identification during spectroscopic classification. In some implementations, one or more process blocks of FIG. 10 may be performed by a control device (e.g., control device 210). In some implementations, one or more process blocks of FIG. 10 may be performed by another device or a group of devices separate from or including the control device, such as a spectrometer (e.g., spectrometer 220). Additionally, or alternatively, one or more process blocks of FIG. 10 may be performed by one or more components of device 300, such as processor 320, memory 330, storage component 340, input component 350, output component 360, and/or communication interface 370.

As shown in FIG. 10, process 1000 may include determining that an unknown sample is an outlier sample by using an aggregated classification model (block 1010). For example, the control device may determine that an unknown sample is an outlier sample by using an aggregated classification model, as described above.

As further shown in FIG. 10, process 1000 may include determining that one or more spectroscopic measurements are not performed accurately based on determining that the unknown sample is the outlier sample (block 1020). For example, the control device may determine that one or more spectroscopic measurements are not performed accurately based on determining that the unknown sample is the outlier sample, as described above.

As further shown in FIG. 10, process 1000 may include causing one or more actions based on determining the one or more spectroscopic measurements are not performed accurately (block 1030). For example, the control device may cause one or more actions based on determining the one or more spectroscopic measurements are not performed accurately, as described above.

Process 1000 may include additional implementations, such as any single implementation or any combination of implementations described below and/or in connection with one or more other processes described elsewhere herein.

In a first implementation, causing the one or more actions comprises providing output indicating that the outlier sample is included in a no-match class.

In a second implementation, process 1000 includes performing a prediction using the dataset based on removing the data corresponding to the outlier sample, and providing output identifying a result of the prediction.

In a third implementation, determining that the unknown sample is an outlier sample comprises determining that the unknown sample is an outlier sample using a median absolute deviation technique.

In a fourth implementation, determining that the unknown sample is an outlier sample comprises determining that the unknown sample is an outlier sample using Grubb's test.

In a fifth implementation, process 1000 includes receiving information identifying results of a set of spectroscopic measurements of a training set of known samples and a validation set of known samples, generating the aggregated classification model based on the information identifying the results of the set of spectroscopic measurements, the aggregated classification model including at least one class relating to a material of interest for a spectroscopic determination, the aggregated classification model including a no-match class relating to at least one material that is not of interest or a baseline spectroscopic measurement, receiving information identifying a result of a particular spectroscopic measurement of the unknown sample, generating a local classification model based on the aggregated classification model and the result of the particular spectroscopic measurement of the unknown sample, and where determining that the unknown sample is an outlier sample comprises determining that the unknown sample is an outlier sample based on the local classification model.

In a sixth implementation, generating the local classification model comprises selecting a set of top classes from the aggregated classification model, and generating a set of local classes of the local classification model based on the set of top classes from the aggregated classification model, wherein a particular local class, of the set of local classes, includes the unknown sample.

In a seventh implementation, determining that the unknown sample is an outlier sample comprises determining that the unknown sample is an outlier sample based on an evaluation of the unknown sample relative to the particular local class.

In an eighth implementation, determining that the unknown sample is an outlier sample comprises determining that the unknown sample is an outlier sample based on an evaluation of the unknown sample relative to the set of local classes.

In a ninth implementation, process 1000 includes receiving information identifying results of a set of spectroscopic measurements of a training set of known samples and a validation set of known samples, generating a classification model based on the information identifying the results of the set of spectroscopic measurements, the classification model including at least one class relating to a material of interest for a spectroscopic determination, the classification model including a no-match class relating to at least one material that is not of interest or a baseline spectroscopic measurement, receiving information identifying a particular result of a particular spectroscopic measurement of an unknown sample, performing a first evaluation of the classification model on the unknown sample, identifying, based on the first evaluation, an outlier sample is present in the classification model, removing the outlier sample from the classification model, performing a second evaluation of the classification model on the unknown sample based on removing the outlier sample from the classification model, and providing output indicating whether the unknown sample is included in the no-match class based on performing the second evaluation of the classification model.

In a tenth implementation, process 1000 includes providing output identifying a class to which the unknown sample is classified.

In an eleventh implementation, the classification model is a first classification model, and further comprising performing, using the first classification model, a first classification to identify a set of local classes, of the first classification model, for the particular spectroscopic measurement, generating a second classification model based on the set of local classes, the second classification model including the no-match class, and performing a second classification using the second classification model to determine whether the unknown sample is included in the no-match class.

In a twelfth implementation, process 1000 includes identifying the outlier sample from the set of local classes of the second classification model.

In a thirteenth implementation, process 1000 includes determining that a first confidence measure of the first evaluation does not satisfy a threshold, and performing the second evaluation based on determining that the first confidence measure does not satisfy the threshold.

In a fourteenth implementation, process 1000 includes determining that a second confidence measure of the second evaluation does satisfy the threshold, and providing the output based on determining that the second confidence measure does satisfy the threshold.

In a fifteenth implementation, process 1000 includes receiving information identifying results of a spectroscopic measurement performed on an unknown sample, aggregating a plurality of classes of a classification model to generate an aggregated classification model, determining that the spectroscopic measurement is performed accurately using the aggregated classification model, determining a confidence measure for a set of classes of the aggregated classification model, selecting a subset of the set of classes based on the confidence measure for the set of classes, generating an in situ local classification model using the subset of the set of classes, identifying one or more outlier samples in the in situ local classification model, removing the one or more outlier samples from the in situ local classification model, generating a prediction using the in situ local classification model based on removing the one or more outlier samples, and providing an output identifying the prediction.

In a sixteenth implementation, the prediction is an assignment of the unknown sample to a no-match class.

In a seventeenth implementation, the prediction is an assignment of the unknown sample to a class other than a no-match class.

In an eighteenth implementation, process 1000 includes removing a plurality of samples using an iterative evaluation of whether each sample, of the plurality of samples, is an outlier sample in the in situ local classification model.

In a nineteenth implementation, process 1000 includes removing a plurality of samples using a concurrent evaluation of whether each sample, of the plurality of samples, is an outlier sample in the in situ local classification model.

Although FIG. 10 shows example blocks of process 1000, in some implementations, process 1000 may include additional blocks, fewer blocks, different blocks, or differently arranged blocks than those depicted in FIG. 10. Additionally, or alternatively, two or more of the blocks of process 1000 may be performed in parallel.

In this way, control device 210 reduces a likelihood of providing an inaccurate result of spectroscopy based on avoiding a false positive identification of an unknown sample as being a particular material of interest for which a classification model is trained to identify.

The foregoing disclosure provides illustration and description, but is not intended to be exhaustive or to limit the implementations to the precise form disclosed. Modifications and variations are possible in light of the above disclosure or may be acquired from practice of the implementations.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items and unrelated items, etc.), and may be used interchangeably with "one or more." Where only one item is intended, the term "one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A method, comprising:
receiving, by a device that includes a processor, information identifying results of a set of spectroscopic measurements of a training set of known samples and a validation set of known samples;
causing, by the device, one or more spectrometers to perform one or more spectroscopic measurements of an unknown sample;
receiving, by the device and based on causing the one or more spectrometers to perform the one or more spectroscopic measurements of the unknown sample, information identifying a result of the one or more spectroscopic measurements of the unknown sample; and
causing, by the device, one or more actions based on a local classification model indicating that the unknown sample is an outlier sample,
the local classification model being based on an aggregated classification model and the result of the one or more spectroscopic measurements of the unknown sample, and
the aggregated classification model being based on the information identifying the results of the set of spectroscopic measurements of the training set and the validation set.

2. The method of claim 1, wherein the aggregated classification model includes at least one class relating to a material of interest for a spectroscopic determination.

3. The method of claim 1, wherein the aggregated classification model includes a no-match class relating to at least one of at least one material that is not of interest or a baseline spectroscopic measurement.

4. The method of claim 1, further comprising:
selecting a set of top classes from the aggregated classification model; and generating the local classification model by generating a set of local classes of the local classification model based on the set of top classes from the aggregated classification model,
wherein a particular local class, of the set of local classes, includes the unknown sample.

5. The method of claim 4, further comprising:
determining that the local classification model indicates that the unknown sample is the outlier sample based on an evaluation of the unknown sample relative to the particular local class or the set of local classes.

6. The method of claim 1, wherein causing the one or more actions comprises:
providing output indicating that the outlier sample is included in a no-match class.

7. A system, comprising:
one or more memories; and
one or more processors, coupled to the one or more memories, configured to:
receive information identifying results of a set of spectroscopic measurements;
cause one or more spectrometers to perform one or more spectroscopic measurements of an unknown sample;
receive, based on the one or more spectrometers being caused to perform the one or more spectroscopic measurements of the unknown sample, information identifying a result of the one or more spectroscopic measurements of the unknown sample; and
cause one or more actions based on a local classification model indicating that the unknown sample is an outlier sample,
the local classification model being based on an aggregated classification model and the result of the one or more spectroscopic measurements of the unknown sample, and
the aggregated classification model being based on the information identifying the results of the set of spectroscopic measurements.

8. The system of claim 7, wherein the aggregated classification model includes at least one class relating to a material of interest for a spectroscopic determination.

9. The system of claim 7, wherein the aggregated classification model includes a no-match class relating to at least one of at least one material that is not of interest or a baseline spectroscopic measurement.

10. The system of claim 7, wherein the one or more processors are further configured to:
select a set of top classes from the aggregated classification model; and
generate the local classification model by generating a set of local classes of the local classification model based on the set of top classes from the aggregated classification model,
wherein a particular local class, of the set of local classes, includes the unknown sample.

11. The system of claim 10, wherein the one or more processors are further configured to:
determine that the local classification model indicates that the unknown sample is the outlier sample based on an evaluation of the unknown sample relative to the particular local class.

12. The system of claim 7, wherein the one or more processors are further configured to:

determine that the local classification model indicates that the unknown sample is the outlier sample based on an evaluation of the unknown sample relative to the set of local classes.

13. The system of claim 7, wherein the one or more processors, to cause the one or more actions, are configured to:

provide output indicating that the outlier sample is included in a no-match class.

14. A non-transitory computer-readable medium storing a set of instructions, the set of instructions comprising:

one or more instructions that, when executed by one or more processors, cause the one or more processors to:

receive information identifying results of a set of spectroscopic measurements of a training set of known samples and a validation set of known samples;

cause one or more spectrometers to perform one or more spectroscopic measurements of an unknown sample;

receive, based on the one or more spectrometers being caused to perform the one or more spectroscopic measurements of the unknown sample, information identifying a result of the one or more spectroscopic measurements of the unknown sample; and cause one or more actions based on a local classification model indicating information regarding the unknown sample, the local classification model being based on an aggregated classification model and the result of the one or more spectroscopic measurements of the unknown sample, and the aggregated classification model being based on the information identifying the results of the set of spectroscopic measurements of the training set and the validation set.

15. The non-transitory computer-readable medium of claim 14, wherein the aggregated classification model includes at least one class relating to a material of interest for a spectroscopic determination.

16. The non-transitory computer-readable medium of claim 14, wherein the aggregated classification model includes a no-match class relating to at least one of at least one material that is not of interest or a baseline spectroscopic measurement.

17. The non-transitory computer-readable medium of claim 14, wherein the one or more instructions further cause the one or more processors to:

generate the local classification model by generating a set of local classes of the local classification model; and determine that the local classification model indicates that the unknown sample is an outlier sample based on an evaluation of the unknown sample relative to the set of local classes.

18. The method of claim 1, further comprising:

causing the one or more spectrometers to perform the set of spectroscopic measurements of the training set and the validation set, wherein the information identifying the results of the set of spectroscopic measurements of the training set and the validation set are received based on causing the one or more spectrometers to perform the set of spectroscopic measurements of the training set and the validation set.

19. The system of claim 7, wherein the one or more processors are further configured to:

cause the one or more spectrometers to perform the set of spectroscopic measurements on a training set of known samples and a validation set of known samples; and wherein the one or more processors, to receive the information identifying the results of the set of spectroscopic measurements, are configured to:

receive the information identifying the results of the set of spectroscopic measurements based on the set of spectroscopic measurements being performed on the training set and the validation set.

20. The non-transitory computer-readable medium of claim 14, wherein the one or more instructions further cause the one or more processors to:

cause the one or more spectrometers to perform the set of spectroscopic measurements of the training set and the validation set.

*        *        *        *        *